United States Patent
Charrier et al.

(10) Patent No.: US 9,827,185 B2
(45) Date of Patent: *Nov. 28, 2017

(54) DYEING COMPOSITION COMPRISING AT LEAST ONE FATTY SUBSTANCE, AT LEAST ONE OXIDIZING AGENT AND AT LEAST ONE NON-IONIC, ANIONIC AND AMPHOTERIC SURFACTANT

(71) Applicant: L'OREAL, Paris (FR)

(72) Inventors: Delphine Charrier, Boulogne Billancourt (FR); Geraldine Fack, Levallois (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/418,762

(22) PCT Filed: Aug. 2, 2013

(86) PCT No.: PCT/EP2013/066264
§ 371 (c)(1),
(2) Date: Jan. 30, 2015

(87) PCT Pub. No.: WO2014/020146
PCT Pub. Date: Feb. 6, 2014

(65) Prior Publication Data
US 2015/0202142 A1    Jul. 23, 2015

Related U.S. Application Data

(60) Provisional application No. 61/698,764, filed on Sep. 10, 2012, provisional application No. 61/698,787, filed on Sep. 10, 2012.

(30) Foreign Application Priority Data

Aug. 2, 2012  (FR) ...................................... 12 57537
Aug. 2, 2012  (FR) ...................................... 12 57542

(51) Int. Cl.
| | |
|---|---|
| A61Q 5/10 | (2006.01) |
| A61K 8/92 | (2006.01) |
| A61K 8/31 | (2006.01) |
| A61K 8/39 | (2006.01) |
| A61K 8/86 | (2006.01) |
| A61K 8/22 | (2006.01) |
| A61K 8/44 | (2006.01) |
| A61K 8/46 | (2006.01) |
| A61K 8/73 | (2006.01) |
| A61K 8/81 | (2006.01) |
| A61K 8/41 | (2006.01) |
| B65D 25/04 | (2006.01) |
| B65D 81/32 | (2006.01) |

(52) U.S. Cl.
CPC .................. *A61K 8/92* (2013.01); *A61K 8/22* (2013.01); *A61K 8/31* (2013.01); *A61K 8/39* (2013.01); *A61K 8/415* (2013.01); *A61K 8/442* (2013.01); *A61K 8/463* (2013.01); *A61K 8/737* (2013.01); *A61K 8/817* (2013.01); *A61K 8/86* (2013.01); *A61Q 5/10* (2013.01); *B65D 25/04* (2013.01); *B65D 81/32* (2013.01); *A61K 2800/4324* (2013.01); *A61K 2800/596* (2013.01); *A61K 2800/882* (2013.01)

(58) Field of Classification Search
CPC ... A61Q 5/10; A61K 8/38; A61K 8/22; A61K 8/92; A61K 8/415; A61K 8/817; A61K 8/463; A61K 8/32; A61K 2800/596; A61K 2800/882; A61K 2800/4324
USPC .......................................................... 8/405
See application file for complete search history.

(56) References Cited

U.S. PATENT DOCUMENTS

| | | | |
|---|---|---|---|
| 2,261,002 | A | 10/1941 | Ritter |
| 2,271,378 | A | 1/1942 | Searle |
| 2,273,780 | A | 2/1942 | Dittmar |
| 2,375,853 | A | 5/1945 | Kirby et al. |
| 2,388,614 | A | 11/1945 | Kirby et al. |
| 2,454,547 | A | 11/1948 | Bock et al. |
| 2,798,053 | A | 7/1957 | Brown |

(Continued)

FOREIGN PATENT DOCUMENTS

| | | |
|---|---|---|
| CN | 1111444 A | 11/1995 |
| CN | 1308931 A | 8/2001 |

(Continued)

OTHER PUBLICATIONS

STIC Search Report dated Nov. 4, 2015.*
English language Abstract for FR 2886136A1 (EP1728500) (Dec. 1, 2006).
English language Abstract for FR 2940066A1 (Jun. 25, 2010).
English language Abstract for JP 02-019576A (Jan. 23, 1990).
English language Abstract for JP 05-163124A (Jun. 29, 1993).
Porter, M.R., "Handbook of Surfactants," published by Blackie & Son (Glasgow and London), 1991, pp. 116-178.
Todd, Charles, et al., "Volatile Silicone Fluids for Cosmetic Formulations," Cosmetics and Toiletries, vol. 91, Jan. 1976, pp. 29-32.
International Search Report and Written Opinion for PCT/EP2013/066268, dated Sep. 25, 2013.

(Continued)

*Primary Examiner* — Eisa Elhilo
(74) *Attorney, Agent, or Firm* — The Marbury Law Group, PLLC

(57) ABSTRACT

The subject of the present invention is a composition for dyeing human keratin fibres such as the hair, comprising: (a) at least one colouring agent chosen from oxidation dye precursors, direct dyes and mixtures thereof; (b) at least one amphoteric or zwitterionic surfactant; (c) at least one non-ionic surfactant; (d) at least one anionic surfactant (e) one or more fatty substances at a total content of at least 10% by weight relative to the weight of the composition; (f) at least one cationic polymer; (g) at least one oxidizing agent other than atmospheric oxygen. The present invention also relates to a process for dyeing human keratin fibres, in which this composition is applied to said fibres, and also to a suitable multicompartment device.

18 Claims, No Drawings

(56) References Cited

U.S. PATENT DOCUMENTS

| | | |
|---|---|---|
| 2,923,692 A | 2/1960 | Ackerman et al. |
| 2,961,347 A | 11/1960 | Floyd |
| 3,100,739 A | 8/1963 | Kaiser et al. |
| 3,206,462 A | 9/1965 | McCarty |
| 3,227,615 A | 1/1966 | Korden |
| 3,524,842 A | 8/1970 | Grossmann et al. |
| 3,578,386 A | 5/1971 | Kalopissis et al. |
| 3,589,978 A | 6/1971 | Kamal et al. |
| 3,617,163 A | 11/1971 | Kalopissis et al. |
| 3,632,559 A | 1/1972 | Matter et al. |
| 3,665,036 A | 5/1972 | Kalopissis et al. |
| 3,709,437 A | 1/1973 | Wright |
| 3,817,698 A | 6/1974 | Kalopissis et al. |
| 3,867,456 A | 2/1975 | Kalopissis et al. |
| 3,869,454 A | 3/1975 | Lang et al. |
| 3,874,870 A | 4/1975 | Green et al. |
| 3,910,862 A | 10/1975 | Barabas et al. |
| 3,912,808 A | 10/1975 | Sokol |
| 3,915,921 A | 10/1975 | Schlatzer, Jr. |
| 3,917,817 A | 11/1975 | Vanlerberghe et al. |
| 3,929,990 A | 12/1975 | Green et al. |
| 3,937,364 A | 2/1976 | Wright |
| 3,955,918 A | 5/1976 | Lang |
| 3,966,904 A | 6/1976 | Green et al. |
| 3,985,499 A | 10/1976 | Lang et al. |
| 3,986,825 A | 10/1976 | Sokol |
| 4,001,432 A | 1/1977 | Green et al. |
| 4,003,699 A | 1/1977 | Rose et al. |
| 4,005,193 A | 1/1977 | Green et al. |
| 4,013,787 A | 3/1977 | Varlerberghe et al. |
| 4,022,351 A | 5/1977 | Wright |
| 4,025,301 A | 5/1977 | Lang |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,147,306 A | 4/1979 | Bennett |
| 4,151,162 A | 4/1979 | Lang et al. |
| 4,157,388 A | 6/1979 | Christiansen |
| 4,165,367 A | 8/1979 | Chakrabarti |
| 4,166,894 A | 9/1979 | Schaper |
| 4,172,887 A | 10/1979 | Vanlerberghe et al. |
| RE30,199 E | 1/1980 | Rose et al. |
| 4,184,615 A | 1/1980 | Wright |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,223,009 A | 9/1980 | Chakrabarti |
| 4,226,784 A | 10/1980 | Kalopissis et al. |
| 4,237,243 A | 12/1980 | Quack et al. |
| 4,277,581 A | 7/1981 | Vanlerberghe et al. |
| 4,348,202 A | 9/1982 | Grollier et al. |
| 4,349,532 A | 9/1982 | Vanlerberghe et al. |
| 4,381,919 A | 5/1983 | Jacquet et al. |
| 4,422,853 A | 12/1983 | Jacquet et al. |
| 4,509,949 A | 4/1985 | Huang et al. |
| 4,579,732 A | 4/1986 | Grollier et al. |
| 4,591,610 A | 5/1986 | Grollier |
| 4,598,862 A | 7/1986 | Rice |
| 4,608,250 A | 8/1986 | Jacquet et al. |
| 4,615,467 A | 10/1986 | Grogan et al. |
| 4,702,906 A | 10/1987 | Jacquet et al. |
| 4,719,282 A | 1/1988 | Nadolsky et al. |
| 4,761,273 A | 8/1988 | Grollier et al. |
| 4,777,040 A | 10/1988 | Grollier et al. |
| 4,804,385 A | 2/1989 | Grollier et al. |
| 4,886,517 A | 12/1989 | Bugaut et al. |
| 4,948,579 A | 8/1990 | Jacquet et al. |
| 4,970,066 A | 11/1990 | Grollier et al. |
| 5,061,289 A | 10/1991 | Clausen et al. |
| 5,196,189 A | 3/1993 | Jacquet et al. |
| 5,364,031 A | 11/1994 | Taniguchi et al. |
| 5,380,340 A | 1/1995 | Neunhoeffer et al. |
| 5,422,031 A | 6/1995 | Nomura et al. |
| 5,534,267 A | 7/1996 | Neunhoeffer et al. |
| 5,663,366 A | 9/1997 | Neunhoeffer et al. |
| 5,670,471 A | 9/1997 | Amalric et al. |
| 5,685,882 A | 11/1997 | Samain et al. |
| 5,708,151 A | 1/1998 | Mockli |
| 5,733,343 A | 3/1998 | Mockli |
| 5,766,576 A | 6/1998 | Lowe et al. |
| 5,879,413 A | 3/1999 | Pengilly et al. |
| 5,888,252 A | 3/1999 | Mockli |
| 5,919,273 A | 7/1999 | Rondeau et al. |
| 5,944,360 A | 8/1999 | Crapart |
| 5,993,490 A | 11/1999 | Rondeau et al. |
| 6,045,591 A | 4/2000 | Deneulenaere |
| 6,099,592 A | 8/2000 | Vidal et al. |
| 6,120,780 A | 9/2000 | Dupuis et al. |
| 6,136,042 A | 10/2000 | Maubru |
| 6,179,881 B1 | 1/2001 | Henrion et al. |
| 6,284,003 B1 | 9/2001 | Rose et al. |
| 6,338,741 B1 | 1/2002 | Vidal et al. |
| 6,458,167 B1 | 10/2002 | Genet et al. |
| 6,492,502 B2 | 12/2002 | Henrion et al. |
| 6,497,730 B1 | 12/2002 | Genet et al. |
| 6,645,258 B2 | 11/2003 | Vidal et al. |
| 6,689,922 B1 | 2/2004 | Bernardon |
| 6,730,789 B1 | 5/2004 | Birault et al. |
| 6,797,013 B1 | 9/2004 | Cotteret et al. |
| 6,863,883 B1 | 3/2005 | Tsujino et al. |
| 7,125,427 B2 | 10/2006 | Schmenger et al. |
| 7,879,113 B2 | 2/2011 | Simonet et al. |
| 8,066,781 B2 | 11/2011 | Hercouet et al. |
| 8,147,564 B2 | 4/2012 | Deconinck et al. |
| 8,236,063 B2 | 8/2012 | Reichert et al. |
| 8,889,110 B2 | 11/2014 | Braida-Valerio et al. |
| 2001/0001332 A1 | 5/2001 | Henrion et al. |
| 2002/0010970 A1* | 1/2002 | Cottard ............... A61K 8/342 8/405 |
| 2002/0050013 A1 | 5/2002 | Vidal et al. |
| 2002/0165368 A1 | 11/2002 | Henrion et al. |
| 2002/0184717 A9 | 12/2002 | Cottard et al. |
| 2003/0019051 A9 | 1/2003 | Vidal et al. |
| 2004/0098815 A1 | 5/2004 | Schmenger et al. |
| 2006/0000032 A1 | 1/2006 | Knuebel et al. |
| 2006/0070191 A1 | 4/2006 | Lang et al. |
| 2010/0154136 A1 | 6/2010 | Hercouet et al. |
| 2010/0158844 A1 | 6/2010 | Braida-Valerio et al. |
| 2010/0162493 A1 | 7/2010 | Audousset et al. |
| 2010/0175202 A1* | 7/2010 | Simonet ............... A61K 8/31 8/416 |
| 2010/0247465 A1 | 9/2010 | Simonet et al. |
| 2011/0033407 A1 | 2/2011 | Krueger et al. |
| 2011/0155166 A1 | 6/2011 | Deconinck et al. |
| 2012/0048288 A1 | 3/2012 | Reichert et al. |
| 2012/0276029 A1 | 11/2012 | Ascione et al. |

FOREIGN PATENT DOCUMENTS

| | | |
|---|---|---|
| CN | 101822618 A | 9/2010 |
| DE | 2359399 A1 | 6/1975 |
| DE | 2527638 A1 | 5/1976 |
| DE | 2538363 A1 | 5/1976 |
| DE | 3843892 A1 | 6/1990 |
| DE | 4133957 A1 | 4/1993 |
| DE | 4137005 A1 | 5/1993 |
| DE | 4220388 A1 | 12/1993 |
| DE | 19543988 A1 | 5/1997 |
| DE | 20114179 U1 | 10/2001 |
| DE | 102006012575 A1 | 2/2007 |
| DE | 1020090903002 A1 | 11/2010 |
| DE | 102011017519 A1 | 10/2012 |
| EP | 0080976 A1 | 6/1983 |
| EP | 0122324 A1 | 10/1984 |
| EP | 0173109 A2 | 3/1986 |
| EP | 0216479 A1 | 4/1987 |
| EP | 0395282 A2 | 10/1990 |
| EP | 0503853 A2 | 9/1992 |

(56) References Cited

FOREIGN PATENT DOCUMENTS

| | | |
|---|---|---|
| EP | 0531943 A1 | 3/1993 |
| EP | 0714954 A2 | 6/1996 |
| EP | 0770375 A1 | 5/1997 |
| EP | 0815828 A1 | 1/1998 |
| EP | 0823250 A2 | 2/1998 |
| EP | 0850636 A1 | 7/1998 |
| EP | 0850637 A1 | 7/1998 |
| EP | 0860636 A1 | 8/1998 |
| EP | 0918053 A1 | 5/1999 |
| EP | 0920856 A1 | 6/1999 |
| EP | 1062940 A1 | 12/2000 |
| EP | 1123693 A2 | 8/2001 |
| EP | 1133975 A2 | 9/2001 |
| EP | 2014275 A2 | 1/2009 |
| EP | 2198923 A2 | 6/2010 |
| EP | 2198929 A1 | 6/2010 |
| EP | 2272493 A1 | 1/2011 |
| EP | 2340807 A2 | 7/2011 |
| FR | 1221122 A | 5/1960 |
| FR | 1516943 A | 2/1968 |
| FR | 1540423 A | 8/1968 |
| FR | 1567219 A | 5/1969 |
| FR | 1583363 A | 10/1969 |
| FR | 2077143 A | 10/1971 |
| FR | 2080759 A1 | 11/1971 |
| FR | 2162025 A1 | 7/1973 |
| FR | 2189006 A1 | 1/1974 |
| FR | 2190406 A2 | 2/1974 |
| FR | 2252840 A1 | 6/1975 |
| FR | 2270846 A1 | 12/1975 |
| FR | 2275462 A1 | 1/1976 |
| FR | 2280361 A2 | 2/1976 |
| FR | 2285851 A1 | 4/1976 |
| FR | 2316271 A1 | 1/1977 |
| FR | 2320330 A1 | 3/1977 |
| FR | 2336434 A1 | 7/1977 |
| FR | 2368508 A2 | 5/1978 |
| FR | 2393573 A1 | 1/1979 |
| FR | 2413907 A1 | 8/1979 |
| FR | 2416723 A1 | 9/1979 |
| FR | 2505348 A1 | 11/1982 |
| FR | 2542997 A1 | 9/1984 |
| FR | 2570946 A1 | 4/1986 |
| FR | 2722687 A1 | 1/1996 |
| FR | 1560664 A | 3/1996 |
| FR | 2733749 A1 | 11/1996 |
| FR | 2757385 A1 | 6/1998 |
| FR | 2788433 A1 | 7/2000 |
| FR | 2801308 A1 | 5/2001 |
| FR | 2886136 A1 | 12/2006 |
| FR | 2940066 A1 | 6/2010 |
| FR | 2954092 A1 | 6/2011 |
| FR | 2954095 A1 | 6/2011 |
| GB | 738585 A | 10/1955 |
| GB | 1026978 A | 4/1966 |
| GB | 1153196 A | 5/1969 |
| GB | 1163385 A | 9/1969 |
| GB | 1195386 A | 6/1970 |
| GB | 1514466 A | 6/1978 |
| GB | 1546809 A | 5/1979 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 95/01772 A1 | 1/1995 |
| WO | WO 95/01772 * | 1/1995 ............... A61K 7/13 |
| WO | 95/15144 A1 | 6/1995 |
| WO | 96/15765 A1 | 5/1996 |
| WO | 97/44004 A1 | 11/1997 |
| WO | 98/44012 A1 | 10/1998 |
| WO | 99/36047 A1 | 7/1999 |
| WO | 99/48465 A1 | 9/1999 |
| WO | 00/26167 A1 | 5/2000 |
| WO | 01/66646 A1 | 9/2001 |
| WO | 03/020229 A2 | 3/2003 |
| WO | 03/029359 A1 | 4/2003 |
| WO | 2006/125619 A1 | 11/2006 |
| WO | 2008/049768 A1 | 5/2008 |
| WO | 2010/133640 A2 | 11/2010 |
| WO | 2011/009563 A2 | 1/2011 |
| WO | 2014/020145 A2 | 2/2014 |
| WO | 2014/020147 A1 | 2/2014 |
| WO | 2014/020148 A2 | 2/2014 |
| WO | 2014/08433 A1 | 7/2014 |

OTHER PUBLICATIONS

International Search Report and Written Opinion for co-pending PCT/EP2013/066266 (WO 2014/020147A2), dated May 15, 2014.
International Search Report for co-pending PCT/EP2013/066263 (WO 2014/020145A2), dated Oct. 18, 2013.
International Search Report and Written Opinion for co-pending PCT/EP2013/066264 (WO 2014/020146A2), dated Nov. 4, 2014.
English language abstract for DE 4137005A1 (May 13, 1993).
English language Abstract for DE 4220388A1 (Dec. 23, 1993).
English language Abstract for DE 102006012575A1. (Feb. 8, 2007).
English language Abstract for EP 0080976A1 (Jun. 8, 1983).
English language Abstract for EP 0770375A1 (May 2, 1997).
English language Abstract for EP 1123693A2 (Aug. 16, 2001).
English language Abstract for EP 2014276A2 (Jan. 14, 2009).
International Search Report for counterpart foreign Application PCT/EP2014/0502110, dated May 20, 2014.
Non-Final Office Action for co-pending U.S. Appl. No. 14/418,699, dated Feb. 18, 2016.
Non-Final Office Action for co-pending U.S. Appl. No. 14/418,736, dated Nov. 20, 2015.
Final Office Action for co-pending U.S. Appl. No. 14/418,736, dated Jun. 2, 2016.
Non-Final Office Action for co-pending U.S. Appl. No. 14/418,746, dated Dec. 22, 2015.
Final Office Action for co-pending U.S. Appl. No. 141/418,746, dated Jul. 11, 2016.
Non-Final Office Action for co-pending U.S. Appl. No. 14/758,985, dated Jan. 22, 2016.
Machine translation of First Office Action for counterpart Chinese Application 201380040848.0, dated Feb. 29, 2016.
Machine translation of Second Office Action for counterpart Chinese Application 201380040848.0, dated Nov. 22, 2016.
Machine translation of First Office Action for counterpart Chinese Application 201380040807.1, dated Feb. 2, 2016.
Machine translation of Second Office Action for counterpart Chinese Application 201380040807.1, dated Dec. 16, 2016.
Non-Final Office Action for copending U.S. Appl. No. 14/418,736, dated Dec. 14, 2016.
Final Office Action for copending U.S. Appl. No. 14/418,699, dated Sep. 8, 2016.
Non-Final Office Action for copending U.S. Appl. No. 14/418,746, dated Feb. 16, 2017.
Final Office Action for copending U.S. Appl. No. 14/758,985, dated Jul. 26, 2016.
Non-Final Office Action for copending U.S. Appl. No. 14/758,985, dated Feb. 15, 2017.

* cited by examiner

DYEING COMPOSITION COMPRISING AT LEAST ONE FATTY SUBSTANCE, AT LEAST ONE OXIDIZING AGENT AND AT LEAST ONE NON-IONIC, ANIONIC AND AMPHOTERIC SURFACTANT

This is a national stage application of PCT/EP2013/066264, filed internationally on Aug. 2, 2013, which claims priority to U.S. Provisional Application Nos. 61/698,764 and 61/698,787, both filed on Sep. 10, 2012; as well as French Applications 1257542 and 1257537, both filed on Aug. 2, 2012.

The subject of the present invention is a dyeing composition comprising colouring agents chosen from oxidation dye precursors, direct dyes and mixtures thereof, at least one amphoteric or zwitterionic surfactant, at least one non-ionic surfactant and at least one anionic surfactant, at least 10% by weight of at least one fatty substance and at least one oxidizing agent other than atmospheric oxygen, and also a dyeing process using said composition. The present invention also relates to a suitable multicompartment device.

Among the methods for dyeing human keratin fibres, such as the hair, mention may be made of oxidation dyeing or permanent dyeing. More particularly, this form of dyeing uses one or more oxidation dyes, usually one or more oxidation bases optionally combined with one or more couplers.

In general, the oxidation bases are chosen from ortho- or para-phenylenediamines, ortho or para-aminophenols and heterocyclic compounds. These oxidation bases are colourless or weakly coloured compounds which, when combined with oxidizing products, can give access to coloured entities.

The shades obtained with these oxidation bases are often varied by combining them with one or more couplers, these couplers being chosen especially from aromatic meta-diamines, meta-aminophenols, meta-diphenols and certain heterocyclic compounds, such as indole compounds.

The variety of the molecules used as oxidation bases and couplers allows a rich range of colours to be obtained.

Permanent dyeing processes thus consist in using, with the dye composition containing the oxidation dyes, an aqueous composition comprising at least one oxidizing agent such as hydrogen peroxide, under alkaline pH conditions in the vast majority of cases. The alkaline agent conventionally used is aqueous ammonia or it may be chosen from other alkaline agents, such as alkanolamines.

Recently, dyeing formulations comprising fatty substance contents higher than the compositions thus far on the market have been developed. These formulations provide numerous advantages, in particular in that they make it possible to reduce the aqueous ammonia content, thus providing a very clear improvement in the user's comfort (less of an unpleasant smell and less of a risk of stinging), without any decrease in the dyeing effectiveness being observed, or even with it being increased.

However, such formulations are complex to process precisely because of this high fatty substance content and often result in a deterioration of the use qualities, such as the ease of application and the rinsability.

The objective of the present invention is therefore to improve the use qualities of dye compositions which are in particular in cream form, comprising high fatty substance contents, without causing any decrease in the dyeing effectiveness of such compositions.

This objective and others are achieved by the present invention, the subject of which is thus a composition for dyeing human keratin fibres, such as the hair, comprising:

(a) at least one colouring agent chosen from oxidation dye precursors, direct dyes and mixtures thereof;
(b) at least one amphoteric or zwitterionic surfactant;
(c) at least one non-ionic surfactant;
(d) at least one anionic surfactant;
(e) one or more fatty substances at a total content of at least 10% by weight relative to the weight of the composition;
(f) at least one cationic polymer;
(g) at least one oxidizing agent other than atmospheric oxygen.

The invention also relates to a process for dyeing human keratin fibres in which said composition is applied.

The subject of the invention is also a multicompartment device comprising a compartment containing a composition free of oxidizing agent other than atmospheric oxygen, comprising at least one colouring agent chosen from oxidation dye precursors, direct dyes and mixtures thereof; and a compartment containing an oxidizing composition; both or either of the compositions of the two compartments comprising at least one fatty substance, at least one cationic polymer, at least one amphoteric or zwitterionic surfactant, at least one non-ionic surfactant, at least one anionic surfactant; the two compartments being mixed before use so as to obtain a ready-to-use composition as previously defined.

The composition of the invention makes it possible to obtain good dyeing properties, such as strength of the colour, resistance to external agents (shampooing, perspiration, light) and homogeneity, which are particularly efficient.

It also has a texture suitable for the application. Indeed, the composition according to the invention is easy to apply to the fibres. It rinses off easily after the leave-on time.

Other characteristics and advantages of the invention will emerge more clearly on reading the description and the examples that follow.

In the text hereinbelow, and unless otherwise indicated, the limits of a range of values are included in that range.

The term "at least one" associated with an ingredient of the composition signifies "one or more".

The human keratin fibres treated by means of the process according to the invention are preferably the hair.

Colouring Agents

As indicated previously, the dyeing composition according to the invention comprises at least one colouring agent chosen from oxidation dye precursors, such as oxidation bases and couplers, direct dyes, and mixtures thereof.

Oxidation Dye Precursors

As oxidation dye precursors, use may be made of oxidation bases and couplers.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-6-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl) pyrrolidine, and the addition salts thereof with an acid.

Preference is particularly given, among the abovementioned para-phenylenediamines, to para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine and the addition salts thereof with an acid.

Mention may be made, among bis(phenyl)alkylenediamines, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,6-dioxaoctane and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases, mention may be made, by way of example, of pyridine derivatives, pyrimidine derivatives and pyrazole derivatives.

Mention may be made, among the pyridine derivatives, of the compounds described, for example, in patents GB 1 026 978 and GB 1 153 196, such as 2,5-diaminopyridine, 2-(4-methoxyphenyl)amino-3-aminopyridine, 3,4-diaminopyridine, and the addition salts thereof.

Other pyridine oxidation bases of use in the present invention are the 3-aminopyrazolo[1,5-a]pyridine oxidation bases or addition salts thereof described, for example, in patent application FR 2 801 308. Mention may be made, by way of example, of pyrazolo[1,5-a]pyrid-3-ylamine, 2-(acetylamino)pyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl) methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino] ethanol, 2[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, and the addition salts thereof.

Mention may be made, among pyrimidine derivatives, of the compounds described, for example, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazole derivatives, mention may be made for example of 3,4-diaminopyrazole, 4-amino-1,3-dimethyl-5-hydrazinopyrazole, 1-methyl-3,4,5-triaminopyrazole, 3,5-diamino-1-methyl 4-methylaminopyrazole, 3,5-diamino-4-(β-hydroxyethyl)amino-1-methylpyrazole, and addition salts thereof.

Among the couplers that can be used in the composition employed in the process according to the invention, mention may in particular be made of meta-phenylenediamines, meta-aminophenols, meta-diphenols, naphthalene couplers, heterocyclic couplers such as, for example, indole derivatives, indoline derivatives, sesamol and derivatives thereof, pyridine derivatives, pyrazolotriazole derivatives, pyrazolones, indazoles, benzimidazoles, benzothiazoles, benzoxazoles, 1,3-benzodioxoles, quinolines, and the addition salts of these compounds with an acid.

These couplers are more particularly chosen from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole and 2,6-dimethylpyrazolo[1,5-b]-1,2,4-triazole, the addition salts thereof with an acid, and mixtures thereof.

The addition salts of the oxidation bases and of the couplers are in particular chosen from the addition salts with an acid, such as the hydrochlorides, hydrobromides, sulfates, citrates, succinates, tartrates, lactates, tosylates, benzenesulfonates, phosphates and acetates.

The oxidation base(s) are generally each present in an amount from 0.0001% to 10% by weight relative to the total weight of the composition of the invention, and preferably from 0.005% to 5% by weight relative to the total weight of the composition.

The coupler(s) each generally represent from 0.0001% to 10% by weight relative to the total weight of the composition and preferably from 0.005% to 5% by weight relative to the total weight of the composition of the invention.

Direct Dyes

The term "direct dye" is intended to mean natural and/or synthetic dyes other than oxidation dyes. They are dyes which will spread superficially over the fibre and colour the fibres by themselves.

They may be ionic or non-ionic, preferably cationic or non-ionic.

These direct dyes are, for example, chosen from neutral, acidic or cationic nitrobenzene direct dyes, neutral, acidic or cationic azo direct dyes, tetraazapentamethine dyes, neutral, acidic or cationic quinone and in particular anthroquinone dyes, azine direct dyes, triarylmethane direct dyes, azomethine direct dyes and natural direct dyes.

By way of examples of suitable direct dyes, mention may be made of azo direct dyes; (poly)methine dyes such as cyanins, hemicyanins, and styryl dyes; carbonyl; azine; nitro (hetero)aryl; tri(hetero)arylmethane; porphyrin; phthalocyanine and natural direct dyes, alone or as mixtures.

Preferentially, the direct dye(s) contain(s) at least one quaternized cationic chromophore or at least one chromophore bearing a quaternized or quaternizable cationic group.

According to one particular embodiment of the invention, the direct dyes comprise at least one quaternized cationic chromophore.

By way of direct dye present in the composition according to the invention, mention may be made of the following dyes: acridines; acridones; anthranthrones; anthrapyrimidines; anthraquinones; azines; (poly)azos, hydrazonos or hydrazones, in particular arylhydrazones; azomethines; benzanthrones; benzimidazoles; benzimidazolones; benzindoles; benzoxazoles; benzopyrans; benzothiazoles; benzoquinones; bisazines; bis-isoindolines; carboxanilides; coumarins; cyanines such as azacarbocyanines, diazacarbocyanines, diazahemicyanines, hemicyanines or tetraazacarbocyanines; diazines; diketopyrrolopyrroles; dioxazines; diphenylamines; diphenylmethanes; dithiazines; flavonoides such as flavanthrones and flavones; fluorindines; formazans; indamines; indanthrones; indigoids and pseudo-indigoids; indophenols; indoanilines; isoindolines; isoindolinones; isoviolanthrones; lactones; (poly)methines such as diméthines of stilbene or styryl type; naphthalimides; naphthanilides; naphtholactams; naphthoquinones; nitro, especially nitro (hetero)aromatics; oxadiazoles; oxazines; perilones; perinones; perylenes; phenazines; phenoxazine; phenothiazines; phthalocyanine; polyenes/carotenoides; porphyrins; pyranthrones; pyrazolanthrones; pyrazolones; pyrimidinoanthrones; pyronines; quinacridones; quinolines; quinophthalones; squaranes; tetrazoliums; thiazines, thioindigo; thiopyronines; triarylmethanes or xanthenes.

For the cationic azo dyes, mention may in particular be made of those derived from the cationic dyes described in Kirk Othmer's Encyclopaedia of Chemical Technology, "Dyes, Azo", J. Wiley & sons, updated on 19/04/2010.

Among the azo dyes that can be used according to the invention, mention may be made of the cationic azo dyes described in patent applications WO 95/15144, WO 95/01772 and EP-714954.

According to one preferred embodiment of the invention, the direct dye(s) is (are) chosen from cationic dyes called "basic dyes".

Mention may be made, among the azo dyes described in the Colour Index International 3rd edition, and in particular the following dyes: Basic Red 22, Basic Red 76, Basic Yellow 57, Basic Brown 16 and Basic Brown 17.

Among the cationic quinone dyes, those mentioned in the abovementioned Colour Index International are suitable, and among these, mention may be made, inter alia, of the following dyes: Basic Blue 22 and Basic Blue 99.

Among the azine dyes which are suitable, mention may be made of those listed in the Colour Index International and, for example, the following dyes: Basic Blue 17 and Basic Red 2.

Among the cationic triarylmethane dyes that can be used according to the invention, mention may be made, in addition to those listed in the Colour Index, of the following dyes: Basic Green 1, Basic Violet 3, Basic Violet 14, Basic Blue 7 and Basic Blue 26.

Mention may also be made of the cationic dyes described in documents U.S. Pat. No. 5,888,252, EP 1133975, WO 03/029359, EP 860636, WO 95/01772, WO 95/15144 and EP 714954.

Mention may also be made of those listed in the encyclopaedia "The chemistry of synthetic dyes" by K. Venkataraman, 1952, Academic press Vol 1 to 7, in "Kirk Othmer's Encyclopaedia of Chemical Technology", chapter "Dyes and Dye Intermediates", 1993, Wiley and sons, and in various chapters of "Ullmann's Encyclopaedia of Industrial Chemistry" 7th edition, Wiley and sons.

Preferably, the cationic direct dyes are chosen from those derived from dyes of azo and hydrazono type.

According to one particular embodiment, the direct dyes are cationic azo dyes, as described in EP 850636, FR 2788433, EP 920856, WO 9948465, FR 2757385, EP 850637, EP 918053, WO 9744004, FR 2570946, FR 2285851, DE 2538363, FR 2189006, FR 1560664, FR 1540423, FR 1567219, FR 1516943, FR 1221122, DE 4220388, DE 4137005, WO 0166646, U.S. Pat. No. 5,708, 151, WO 9501772, WO 515144, GB 1195386, U.S. Pat. No. 3,524,842, U.S. Pat. No. 5,879,413, EP 1062940, EP 1133976, GB 738585, DE 2527638, FR 2275462, GB 1974-27645, Acta Histochem. (1978), 61(1), 48-52; Tsitologiya (1968), 10(3), 403-5; Zh. Obshch. Khim. (1970), 40(1), 195-202 ; Ann. Chim. (Rome) (1975), 65(5-6), 305-14; Journal of the Chinese Chemical Society (Taipei) (1998), 45(1), 209-211; Rev. Roum. Chim. (1988), 33(4), 377-83; Text. Res. J. (1984), 54(2), 105-7; Chim. Ind. (Milan) (1974), 56(9), 600-3; Khim. Tekhnol. (1979), 22(5), 548-53; Ger. Monatsh. Chem. (1975), 106(3), 643-8; MRL Bull. Res. Dev. (1992), 6(2), 21-7; Lihua Jianyan, Huaxue Fence (1993), 29(4), 233-4; Dyes Pigm. (1992), 19(1), 69-79; Dyes Pigm. (1989), 11(3), 163-72.

Preferably, the cationic direct dye(s) comprise(s) a quaternary ammonium group, more preferentially the cationic charge is endocyclic.

These cationic radicals are, for example, a cationic radical:
  carrying an exocyclic (di/tri)(C1-C8)alkylammonium charge, or
  carrying an endocyclic charge, such as comprising a cationic heteroaryl group chosen from: acridinium, benzimidazolium, benzobistriazolium, benzopyrazolium, benzopyridazinium, benzoquinolium, benzothiazolium, benzotriazolium, benzoxazolium, bipyridinium, bis-tetrazolium, dihydrothiazolium, imidazopyridinium, imidazolium, indolium, isoquinolium, naphthoimidazolium, naphthooxazolium, naphthopyrazolium, oxadiazolium, oxazolium, oxazolopyridinium, oxonium, phenazinium, phenooxazolium, pyrazinium, pyrazolium, pyrazoyltriazolium, pyridinium, pyridinoimidazolium, pyrrolium, pyrylium, quinolium, tetrazolium, thiadiazolium, thiazolium, thiazolopyridinium, thiazoylimidazolium, thiopyrylium, triazolium or xanthylium.

Mention may be made of the hydrazono cationic dyes of formulae (II) and (III) and the azos of formulae (IV) and (V) below:

 (II)

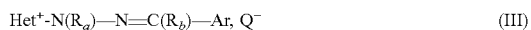 (III)

 (IV)

 (V)

in which formulae (II) to (V):

Het+ represents a cationic heteroaryl radical, preferably carrying an endocyclic cationic charge, such as imidazolium, indolium or pyridinium, which is optionally substituted, preferentially with at least one ($C_1$-$C_8$) alkyl group such as methyl;

Ar+ represents an aryl radical, such as phenyl or naphthyl, carrying an exocyclic cationic charge, preferentially ammonium, particularly tri(C1-C8)alkylammonium, such as trimethylammonium;

Ar represents an aryl group, in particular phenyl, which is optionally substituted, preferentially with one or more electron-donating groups, such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino, or else Ar represents a julolidine group;

Ar" represents a (hetero)aryl group which is optionally substituted, such as phenyl or pyrazolyl which is optionally substituted, preferentially with one or more ($C_1$-$C_8$)alkyl, hydroxyl, (di)($C_1$-$C_8$)(alkyl)amino, ($C_1$-$C_8$)alkoxy or phenyl groups;

$R_a$ and $R_b$, which may be identical or different, represent a hydrogen atom or a ($C_1$-$C_8$)alkyl group which is optionally substituted, preferentially with a hydroxyl group;

or else the substituent $R_a$ with a substituent of Het+ and/or $R_b$ with a substituent of Ar form, together with the atoms which bear them, a (hetero)cycloalkyl; in particular, $R_a$ and $R_b$ represent a hydrogen atom or a ($C_1$-$C_4$)alkyl group which is optionally substituted with a hydroxyl group;

Q− represents an organic or inorganic anionic counterion, such as a halide or an alkyl sulfate.

In particular, mention may be made of the azo and hydrozono direct dyes carrying an endocyclic cationic charge, of formulae (II) to (V), as previously defined; more particularly, the cationic direct dyes of formulae (II) to (V) carrying endocyclic cationic charges, described in patent applications WO 95/15144, WO 95/01772 and EP-714954; preferentially, the following direct dyes:

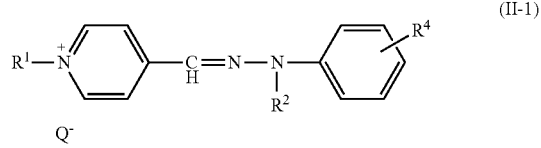 (II-1)

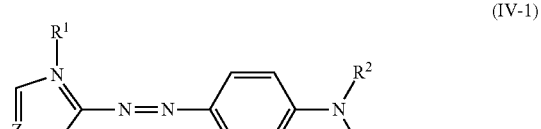 (IV-1)

in which formulae (II-1) and (IV-1):

$R^1$ represents a ($C_1$-$C_4$)alkyl group such as methyl;

$R^2$ and $R^3$, which may be identical or different, represent a hydrogen atom or a ($C_1$-$C_4$)alkyl group such as methyl; and $R^4$ represents a hydrogen atom or an electron-donating group, such as ($C_1$-$C_8$)alkyl which is optionally substituted, ($C_1$-$C_8$)alkoxy which is optionally substituted or (di)($C_1$-$C_8$)(alkyl)amino which is optionally substituted on the alkyl group(s) with a hydroxyl group; in particular, $R^4$ is a hydrogen atom, Z represents a CH group or a nitrogen atom, preferentially CH, Q− is an anionic counterion as previously defined, in particular a halide, such as chloride, or an alkyl sulfate such as methyl sulfate or mesityl.

In particular, the dyes of formulae (II-1) and (IV-1) are chosen from Basic Red 51, Basic Yellow 87 and Basic Orange 31 or derivatives thereof:

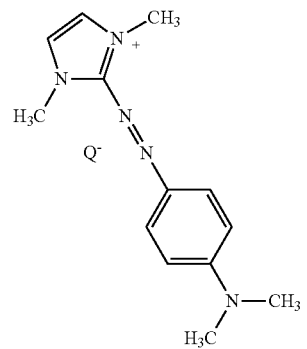

Basic Red 51

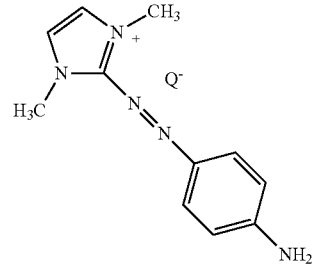

Basic Orange 31

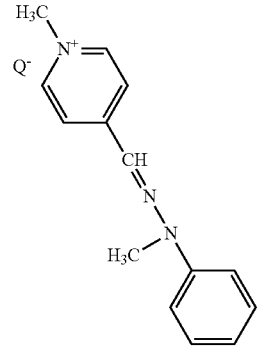

Basic Yellow 87 with Q− an anionic counterion as previously defined, in particular a halide, such as chloride, or an alkyl sulfate such as methyl sulfate or mesityl.

According to one particular embodiment of the invention, the direct dyes are fluorescent, in other words they contain at least one fluorescent chromophore as previously defined.

By way of fluorescent dyes, mention may be made of the radicals resulting from the following dyes: acridines, acridones, benzanthrones, benzimidazoles, benzimidazolones, benzindoles, benzoxazoles, benzopyrans, benzothiazoles, coumarins, difluoro{2-[(2H-pyrrol-2-ylidene-kN)methyl]-1H-pyrrolato-kN}borons (BODIPY®), diketopyrrolopyrroles, fluorindines, (poly)methines (in particular cyanines and styryls/hemicyanines), naphthalimides, naphthanilides, naphthylamines (such as dansyls), oxadiazoles, oxazines, perilones, perinones, perylenes, polyenes/carotenoids, squaranes, stilbenes and xanthenes.

Mention may also be made of the fluorescent dyes described in documents EP 1133975, WO 03/029359, EP 860636, WO 95/01772, WO 95/15144 and EP 714954 and those listed in the encyclopaedia "The Chemistry of Synthetic Dyes" by K. Venkataraman, 1952, Academic press Vol 1 to 7, in the "Kirk Othmer" encyclopaedia of Chemical Technology", chapter "Dyes and Dye Intermediates", 1993, Wiley and sons, and in various chapters of "Ullmann's Encyclopaedia of Industrial Chemistry" 7th edition, Wiley and sons, and in the Handbook—A Guide to Fluorescent Probes and Labelling Technologies, 10th Ed., Molecular Probes/Invitrogen—Oregon 2005, circulated on the Internet or in the preceding printed editions.

According to one preferred variant of the invention, the fluorescent dyes(s) is (are) cationic and comprise(s) at least one quaternary ammonium radical such as those of formula (V) below:

in which formula (V):
W$^+$ represents a cationic heterocyclic or heteroaryl group, in particular comprising a quaternary ammonium optionally substituted with one or more ($C_1$-$C_8$)alkyl groups optionally substituted in particular with one or more hydroxyl groups;
Ar representing an aryl group, such as phenyl or naphthyl, optionally substituted preferentially with i) one or more halogen atoms, such as chlorine or fluorine; ii) one or more ($C_1$-$C_8$)alkyl groups, preferably $C_1$-$C_4$, such as methyl; iii) one or more hydroxyl groups; iv) one or more ($C_1$-$C_8$)alkoxy groups such as methoxy; v) one or more hydroxy ($C_1$-$C_8$)alkyl groups such as hydroxyethyl, vi) one or more amin or (di)($C_1$-$C_8$)alkylamino groups, preferably with the $C_1$-$C_4$ alkyl part optionally substituted with one or more hydroxyls, such as (di)hydroxyethylamino, vii) one or more acylamino groups; viii) one or more heterocycloalkyl groups, such as pyperazinyl or pyperidinyl or heteroaryl groups comprising 5 or 6 ring members, such as pyrrolidinyl, pyridinyl and imidazolinyl;
m' represents an integer inclusively between 1 and 4, in particular m is 1 or 2; more preferentially 1;
$R_c$ and $R_d$, which may be identical or different, represent a hydrogen atom or an optionally substituted ($C_1$-$C_8$) alkyl group, which is preferentially $C_1$-$C_4$, or else $R_c$ contiguous with W$^+$ and/or $R_d$ contiguous with Ar form, with the atoms which bear them, a (hetero) cycloalkyl, in particular $R_c$ is contiguous with W$^+$ and they form a (hetero)cycloalkyl such as cyclohexyl;
Q$^-$ is an organic or inorganic anionic counterion as previously defined.

Among the natural direct dyes that can be used according to the invention, mention may be made of lawsone, juglone, alizarin, purpurin, carminic acid, kermesic acid, purpurogallin, protocatechualdehyde, indigo, isatin, curcumin, spinulosin, apigenidin, haematein, brazilein and orceins. Use may also be made of extracts or decoctions containing natural dyes, and in particular henna-based poultices or extracts.

The direct dye(s) more particularly represent from 0.001% to 10% by weight of the total weight of the composition and preferably from 0.005% to 5% by weight.

Amphoteric or Zwitterionic Surfactants

The dyeing composition according to the invention also comprises at least one amphoteric or zwitterionic surfactant.

In particular, the amphoteric or zwitterionic surfactant(s), which are preferably non-silicone, which are usable in the present invention may especially be derivatives of optionally quaternized aliphatic secondary or tertiary amines, in which derivatives the aliphatic group is a linear or branched chain comprising from 8 to 22 carbon atoms, said amine derivatives containing at least one anionic group, for instance a carboxylate, sulfonate, sulfate, phosphate or phosphonate group.

Mention may be made in particular of ($C_8$-$C_{20}$)alkylbetaines, ($C_8$-$C_{20}$)alkylsulfobetaines, ($C_8$-$C_{20}$)alkylamido($C_3$-$C_8$)alkylbetaines and ($C_8$-$C_{20}$)alkylamido($C_6$-$C_8$)alkylsulfobetaines.

Among the optionally quaternized secondary or tertiary aliphatic amine derivatives that can be used, as defined above, mention may also be made of the compounds of respective structures (B1) and (B2) below:

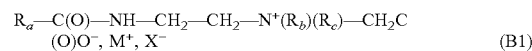

in which formula:
$R_a$ represents a $C_{10}$-$C_{30}$ alkyl or alkenyl group derived from an acid $R_a$—COOH preferably present in hydrolysed coconut oil, or a heptyl, nonyl or undecyl group;
$R_b$ represents a β-hydroxyethyl group; and
$R_c$ represents a carboxymethyl group;
M$^+$ represents a cationic counterion derived from an alkali metal or alkaline-earth metal, such as sodium, an ammonium ion or an ion derived from an organic amine, and
X$^-$ represents an organic or inorganic anionic counterion, such as that chosen from halides, acetates, phosphates, nitrates, ($C_1$-$C_4$)alkyl sulfates, ($C_1$-$C_4$)alkyl- or ($C_1$-$C_4$) alkylarylsulfonates, in particular methyl sulfate and ethyl sulfate; or alternatively M$^+$ and X$^-$ are absent;

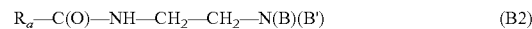

in which formula:
B represents the group —$CH_2$—$CH_2$—O—X';
B' represents the group —$(CH_2)_z$Y', with z=1 or 2;
X' represents the group —$CH_2$—C(O)OH, —$CH_2$—C(O)OZ', —$CH_2$—$CH_2$—C(O)OH, —$CH_2$—$CH_2$—C(O) OZ', or a hydrogen atom;
Y' represents the group —C(O)OH, —C(O)OZ', —$CH_2$—CH(OH)—$SO_3$H or the group —$CH_2$—CH (OH)—$SO_3$—Z';
Z' represents a cationic counterion derived from an alkali metal or alkaline-earth metal, such as sodium, an ammonium ion or an ion derived from an organic amine;
$R_a$' represents a $C_{10}$-$C_{30}$ alkyl or alkenyl group of an acid $R_a$—C(O)OH preferably present in hydrolysed linseed oil or coconut oil, an alkyl group, especially of $C_{17}$ and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium caproamphodiacetate, disodium cocoamphodipropionate, disodium lauroamphodipropionate, disodium caprylamphodipropionate, disodium caproamphodipropionate, lauroamphodipropionic acid and cocoamphodipropionic acid.

By way of example, mention may be made of the cocoamphodiacetate sold by the company Rhodia under the trade name Miranol® C2M Concentrate.

Use may also be made of compounds of formula (B'2):

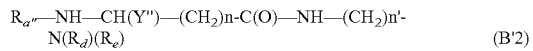

(B'2)

in which formula:

Y″ represents the group —C(O)OH, —C(O)OZ″, —CH$_2$—CH(OH)—SO$_3$H or the group —CH$_2$—CH(OH)—SO$_3$—Z″;

R$_d$ and R$_e$ represent, independently of one another, a C$_1$-C$_4$ alkyl or hydroxyalkyl radical; and Z″ represents a cationic counterion derived from an alkali metal or alkaline-earth metal, such as sodium, an ammonium ion or an ion derived from an organic amine;

R$_{a″}$ represents a C$_{10}$-C$_{30}$ alkyl or alkenyl group of an acid R$_{a″}$—C(O)OH preferably present in hydrolysed linseed oil or coconut oil;

n and n' denote, independently of one another, an integer ranging from 1 to 3.

Among the compounds of formula (B'2), mention may be made of the compound classified in the CTFA dictionary under the name sodium diethylaminopropyl cocoaspartamide and sold by the company Chimex under the name Chimexane HB.

These compounds can be used alone or as mixtures.

Among the amphoteric or zwitterionic surfactants mentioned above, use is preferably made of (C$_8$-C$_{20}$)alkylbetaines such as cocobetaine, (C$_8$-C$_{20}$)alkylamido(C$_3$-C$_8$)alkylbetaines such as cocamidopropylbetaine, and mixtures thereof, and the compounds of formula (B'2), such as the sodium salt of diethylaminopropyl laurylaminosuccinamate (INCI name: sodium diethylaminopropyl cocoaspartamide).

More preferentially, the amphoteric or zwitterionic surfactant(s) are chosen from cocamidopropylbetaine and cocobetaine, the sodium salt of diethylaminopropyl laurylaminosuccinamate, or mixtures thereof.

In accordance with one advantageous embodiment of the invention, the content of amphoteric or zwitterionic surfactant(s) ranges from 0.1% to 30% by weight, preferably from 0.5% to 20% by weight and more preferably from 1% to 10% by weight, relative to the total weight of the composition.

Non-Ionic Surfactants

The composition according to the invention also comprises at least one second surfactant chosen from non-ionic surfactants.

Examples of non-ionic surfactants that may be used in the dye composition used according to the invention are described, for example, in the "Handbook of Surfactants" by M. R. Porter, published by Blackie & Son (Glasgow and London), 1991, pp. 116-178.

By way of examples of additional non-ionic surfactants, mention may be made of oxyalkylenated, or glycerolated, non-ionic surfactants, in particular the following surfactants, alone or as mixtures:

oxyalkylenated (C$_8$-C$_{24}$)alkylphenols;

saturated or unsaturated, linear or branched, oxyalkylenated or glycerolated C$_8$-C$_{30}$ alcohols;

saturated or unsaturated, linear or branched, oxyalkylenated C$_8$-C$_{30}$ fatty acid amides;

esters of saturated or unsaturated, linear or branched, C$_8$-C$_{30}$ acids and of polyethylene glycols;

esters of saturated or unsaturated, linear or branched, C$_8$-C$_{30}$ acids and of sorbitol, which are preferably oxyethylenated;

fatty acid esters of sucrose;

(C$_8$-C$_{30}$)alkylpolyglycosides, (C$_8$-C$_{30}$)alkenylpolyglycosides, which are optionally oxyalkylenated (0 to 10 oxyalkylene units) and which comprise 1 to 15 glucose units, (C$_8$-C$_{30}$)alkylglucoside esters;

oxyethylenated and saturated or unsaturated vegetable oils;

condensates of ethylene oxide and/or of propylene oxide, inter alia, alone or as mixtures;

N—(C$_8$-C$_{30}$)alkylglucamine derivatives and N—(C$_8$-C$_{30}$)acyl-methylglucamine derivatives;

aldobionamides;

amine oxides;

oxyethylenated and/or oxypropylenated silicones.

The oxyalkylene units are more particularly oxyethylene or oxypropylene units, or a combination thereof, preferably oxyethylene units.

The number of moles of ethylene oxide and/or of propylene oxide preferably ranges from 1 to 100, more particularly from 2 to 50; the number of moles of glycerol ranges in particular from 1 to 30.

Advantageously, the non-ionic surfactants do not comprise oxypropylene units.

By way of example of glycerolated non-ionic surfactants, use may preferably be made of monoglycerolated or polyglycerolated C$_8$-C$_{40}$ alcohols comprising from 1 to 30 mol of glycerol, preferably from 1 to 10 mol of glycerol.

By way of example of compounds of this type, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

Among the glycerolated alcohols, it is more particularly preferred to use C$_8$/C$_{10}$ alcohol containing 1 mol of glycerol, C$_{10}$/C$_{12}$ alcohol containing 1 mol of glycerol and C$_{12}$ alcohol containing 1.5 mol of glycerol.

In accordance with a preferred embodiment of the invention, the non-ionic surfactant(s) are chosen from:

oxyethylenated C$_8$-C$_{30}$ alcohols comprising from 1 to 100 mol of ethylene oxide, preferably from 2 to 50, and more particularly from 2 to 30 mol of ethylene oxide;

saturated or unsaturated, oxyethylenated vegetable oils comprising from 1 to 100 mol of ethylene oxide, preferably from 2 to 50;

(C$_8$-C$_{30}$)alkylpolyglycosides, which are optionally oxyalkylenated (0 to 10 OE) and which comprise 1 to 15 glucose units;

monoglycerolated or polyglycerolated C$_8$-C$_{40}$ alcohols comprising from 1 to 30 mol of glycerol, preferably from 1 to 10 mol of glycerol;

saturated or unsaturated, linear or branched, oxyalkylenated C$_8$-C$_{30}$ fatty acid amides;

and mixtures thereof.

Advantageously, the content of non-ionic surfactant(s) ranges from 0.1% to 30% by weight, preferably from 1% to 20% by weight and more preferably from 1% to 10% by weight, relative to the total weight of the composition.

Anionic Surfactants

The composition according to the invention also comprises at least one third category of surfactants, chosen from anionic surfactants. The term "anionic surfactant" is intended to mean a surfactant comprising, as ionic or ionizable groups, only anionic groups. These anionic groups are preferably chosen from the groups —C(O)OH, —C(O)O$^-$, —SO$_3$H, —S(O)$_2$O$^-$, —OS(O)$_2$OH, —OS(P)$_2$O$^-$, —P(O)OH$_2$, —P(O)$_2$O$^-$, —P(O)O$_2$, —P(OH)$_2$, =P(O)OH, —P(OH)O$^-$, =P(O)O$^-$, =POH and =PO$^-$, the anionic parts comprising a cationic counterion such as an alkali metal, an alkaline-earth metal or an ammonium.

By way of examples of additional anionic surfactants that may be used in the dye composition according to the invention, mention may be made of alkyl sulfates, alkyl ether sulfates, alkylamido ether sulfates, alkylaryl polyether sulfates, monoglyceride sulfates, alkyl sulfonates, alkylamide sulfonates, alkylaryl sulfonates, alpha-olefin sulfonates, paraffin sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N-acyl taurates, salts of alkyl monoesters of polyglycoside-polycarboxylic acids, acyl lactylates, salts of D-galactoside uronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds comprising from 6 to 40 carbon atoms and the aryl group denoting a phenyl group.

These compounds can be oxyethylenated and then preferably comprise from 1 to 50 ethylene oxide units.

The salts of $C_6$-$C_{24}$ alkyl monoesters of polyglycoside-polycarboxylic acids can be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, it/they may be chosen from alkali metal salts such as the sodium or potassium salt and preferably the sodium salt, ammonium salts, amine salts and in particular amino alcohol salts or alkaline-earth metal salts such as the magnesium salts.

By way of examples of amino alcohol salts, mention may in particular be made of monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts, and in particular sodium or magnesium salts, are preferably used.

Use is preferably made, among the additional anionic surfactants mentioned, of ($C_6$-$C_{24}$)alkyl sulfates, ($C_6$-$C_{24}$) alkyl ether sulfates comprising from 2 to 50 ethylene oxide units, in particular in the form of alkali metal, ammonium, amino alcohol and alkaline-earth metal salts, or a mixture of these compounds.

In particular, it is preferable to use ($C_{12}$-$C_{20}$)alkyl sulfates, ($C_{12}$-$C_{20}$)alkyl ether sulfates comprising from 2 to 20 ethylene oxide units, in particular in the form of alkali metal, ammonium, amino alcohol and alkaline-earth metal salts, or a mixture of these compounds. Better still, it is preferred to use sodium lauryl ether sulfate containing 2.2 mol of ethylene oxide.

According to one particular embodiment of the invention, the content of non-ionic or anionic surfactant(s) ranges from 0.1% to 30% by weight, preferably from 1% to 20% by weight and more preferably from 1% to 10% by weight, relative to the total weight of the composition.

Preferably, the weight ratio of amphoteric surfactant(s)/anionic surfactant(s) advantageously ranges from 0.1 to 10, more particularly from 0.5 to 5 and preferably from 1 to 3.

In addition, advantageously, the weight ratio of anionic surfactant(s)/non-ionic surfactant(s) advantageously ranges from 0.01 to 5, more particularly from 0.05 to 1 and preferably from 0.1 to 0.5.

It should be noted that, preferably, the weight ratio of non-ionic surfactant(s)/amphoteric or zwitterionic surfactant(s) advantageously ranges from 0.1 to 10, more particularly from 0.5 to 5 and preferably from 1 to 3.

Fatty Substances

As has been mentioned, the composition of the invention comprises one or more fatty substances, the fatty substance content in the composition being at least 10% by weight relative to the weight of the composition.

The term "fatty substance" is intended to mean an organic compound that is insoluble in water at ordinary temperature (25° C.) and at atmospheric pressure (760 mmHg) (solubility of less than 5%, preferably less than 1% and even more preferentially less than 0.1%). They exhibit, in their structure, at least one hydrocarbon-based chain comprising at least 6 carbon atoms or a sequence of at least two siloxane groups. In addition, fatty substances are generally soluble in organic solvents under the same temperature and pressure conditions, such as, for example, chloroform, dichloromethane, carbon tetrachloride, ethanol, benzene, toluene, tetrahydrofuran (THF), liquid petroleum jelly or decamethylcyclopentasiloxane.

The fatty substances of the invention do not comprise salified carboxylic acid groups.

Moreover, the fatty substances of the invention are not (poly)oxyalkylenated or (poly)glycerolated ethers.

The term "oil" is intended to mean a "fatty substance" that is liquid at ambient temperature (25° C.) and at atmospheric pressure (760 mmHg).

The term "non-silicone oil" is intended to mean an oil not containing any silicon (Si) atoms and the term "silicone oil" is intended to mean an oil containing at least one silicon atom.

More particularly, the fatty substances are chosen from $C_6$-$C_{16}$ hydrocarbons, hydrocarbons containing more than 16 carbon atoms, non-silicone oils of animal origin, plant oils of triglyceride type, synthetic triglycerides, fluoro oils, fatty alcohols, fatty acid and/or fatty alcohol esters other than triglycerides and plant waxes, non-silicone waxes and silicones, and mixtures thereof.

It should be remembered that fatty alcohols, esters and acids more particularly exhibit at least one saturated or unsaturated and linear or branched hydrocarbon-based group which comprises from 6 to 30 and better still from 8 to 30 carbon atoms and which is optionally substituted, in particular with one or more hydroxyl groups (in particular 1 to 4). If they are unsaturated, these compounds may comprise one to three conjugated or unconjugated carbon-carbon double bonds.

As regards the $C_6$-$C_{16}$ hydrocarbons, they are linear, branched or optionally cyclic, and are preferably alkanes. Mention may be made, by way of example, of hexane, dodecane or isoparaffins, such as isohexadecane or isodecane.

Mention may be made, as hydrocarbon-based oils of animal origin, of perhydrosqualene.

The triglyceride oils of plant or synthetic origin are preferably chosen from liquid fatty acid triglycerides comprising from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil.

The linear or branched hydrocarbons of inorganic or synthetic origin having more than 16 carbon atoms are preferably chosen from liquid paraffins, petroleum jelly, liquid petroleum jelly, polydecenes or hydrogenated polyisobutene, such as Parleam®.

As regards the $C_6$-$C_{16}$ alkanes, they are linear, branched or optionally cyclic. By way of example, mention may be made of hexane, dodecane and isoparaffins such as isohexadecane and isodecane.

As oils of animal, plant, mineral or synthetic origin that may be used in the composition of the invention, examples that may be mentioned include: fluoro oils which may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or alternatively bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols which are suitable for the implementation of the invention are more particularly chosen from saturated or unsaturated and linear or branched alcohols comprising from 6 to 30 carbon atoms and preferably from 8 to 30 carbon atoms. Mention may be made, for example, of cetyl alcohol, stearyl alcohol and their mixture (cetearyl alcohol), octyldodecanol, 2-butyloctanol, 2-hexyldecanol, 2-undecylpentadecanol, oleyl alcohol or linoleyl alcohol.

As regards the fatty acid and/or fatty alcohol esters, which are advantageously different from the triglycerides mentioned above, mention may be made in particular of esters of saturated or unsaturated and linear or branched $C_1$-$C_{26}$ aliphatic monoacids or polyacids and of saturated or unsaturated and linear or branched $C_1$-$C_{26}$ aliphatic monoalcohols or polyalcohols, the total carbon number of the esters being greater than or equal to 6 and more advantageously greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oeyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate; hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may in particular be made of: diethyl sebacate; diisopropyl sebacate; diisopropyl adipate; di(n-propyl) adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, use is preferably made of ethyl, isopropyl, myristyl, cetyl or stearyl palmitate, 2-ethylhexyl palmitate, 2-octyldecyl palmitate, alkyl myristates, such as isopropyl, butyl, cetyl or 2-octyldodecyl myristate, hexyl stearate, butyl stearate, isobutyl stearate, dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" is intended to mean oxygen-bearing hydrocarbon-based compounds which have several alcohol functions, with or without aldehyde or ketone functions, and which comprise at least 4 carbon atoms. These sugars can be monosaccharides, oligosaccharides or polysaccharides.

Mention may be made, as suitable sugars, for example, of sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar esters of fatty acids may be chosen in particular from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant can also be chosen from mono-, di-, tri- and tetraesters, polyesters, and mixtures thereof.

These esters can, for example, be oleates, laurates, palmitates, myristates, behenates, cocoates, stearates, linoleates, linolenates, caprates, arachidonates or mixtures thereof, such as, in particular, oleate/palmitate, oleate/stearate or palmitate/stearate mixed esters.

More particularly, use is made of monoesters and diesters and in particular mono- or di-oleate, -stearate, -behenate, -oleate/palmitate, -linoleate, -linolenate or -oleate/stearate of sucrose, of glucose or of methylglucose.

An example that may be mentioned is the product sold under the name Glucate® DO by the company Amerchol, which is a methylglucose dioleate.

Examples of esters or mixtures of esters of sugar and of fatty acid that may also be mentioned include:
the products sold under the names F160, F140, F110, F90, F70 and SL40 by the company Crodesta, respectively denoting sucrose palmitate/stearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name Ryoto Sugar Esters, for example referenced B370 and corresponding to sucrose behenate formed from 20% monoester and 80% diester-triester-polyester;

the sucrose monopalmitate/stearate-dipalmitate/stearate sold by the company Goldschmidt under the name Tegosoft® PSE.

The non-silicone wax(es) are chosen in particular from carnauba wax, candelilla wax, esparto wax, paraffin wax, ozokerite, plant waxes, such as olive tree wax, rice wax, hydrogenated jojoba wax or absolute flower waxes, such as the blackcurrant blossom essential wax sold by the company Bertin (France), or animal waxes, such as beeswaxes or modified beeswaxes (cerabellina); other waxes or waxy starting materials which can be used according to the invention are in particular marine waxes, such as that sold by the company Sophim under the reference M82, polyethylene waxes or polyolefin waxes in general.

The silicones that can be used in the dye composition according to the present invention are volatile or non-volatile, cyclic, linear or branched silicones, which are unmodified or modified by organic groups, having a viscosity from $5\times10^{-6}$ to 2.5 m$^2$/s at 25° C., and preferably $1\times10^{-6}$ to 1 m$^2$/s.

The silicones that may be used in accordance with the invention may be in the form of oils, waxes, resins or gums.

Preferably, the silicone is chosen from polydialkylsiloxanes, in particular polydimethylsiloxanes (PDMSs), and organomodified polysiloxanes comprising at least one functional group chosen from amino groups and alkoxy groups.

Organopolysiloxanes are defined in greater detail in Walter Noll's "Chemistry and Technology of Silicones" (1968), Academic Press. They can be volatile or non-volatile.

When they are volatile, the silicones are more particularly chosen from those having a boiling point of between 60° C. and 260° C., and more particularly still from:

(i) cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

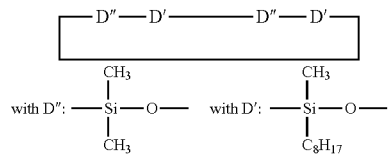

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5\times10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, Jan. 76, pp. 27-32, Todd & Byers, "Volatile Silicone Fluids for Cosmetics".

Use is preferably made of non-volatile polydialkylsiloxanes, polydialkylsiloxane gums and resins, polyorganosiloxanes modified with the organofunctional groups above, and mixtures thereof.

These silicones are more particularly chosen from polydialkylsiloxanes, among which mention may be made mainly of polydimethylsiloxanes having trimethylsilyl end groups. The viscosity of the silicones is measured at 25° C. according to Standard ASTM 445 Appendix C.

Mention may be made, among these polydialkylsiloxanes, without limitation, of the following commercial products:

the Silbione® oils of the 47 and 70 047 series or the Mirasil® oils sold by Rhodia, such as, for example, the oil 70 047 V 500 000;

the oils of the Mirasil® series sold by the company Rhodia;

the oils of the 200 series from the company Dow Corning, such as DC200 with a viscosity of 60 000 mm$^2$/s;

the Viscasil® oils from General Electric and certain oils of the SF series (SF 96, SF 18) from General Electric.

Mention may also be made of polydimethylsiloxanes having dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are polydi($C_1$-$C_{20}$)alkylsiloxanes.

The silicone gums that may be used in accordance with the invention are in particular polydialkylsiloxanes and preferably polydimethylsiloxanes with high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane, tridecane or their mixtures.

Products which can be used more particularly in accordance with the invention are mixtures such as:

the mixtures formed from a polydimethylsiloxane hydroxylated at the chain end, or dimethiconol (CTFA), and from a cyclic polydimethylsiloxane, also known as cyclomethicone (CTFA), such as the product Q2 1401 sold by the company Dow Corning;

the mixtures of a polydimethylsiloxane gum and of a cyclic silicone, such as the product SF 1214 Silicone Fluid from General Electric; this product is a gum SF 30 corresponding to a dimethicone, having a number-average molecular weight of 500 000, dissolved in the oil SF 1202 Silicone Fluid corresponding to decamethylcyclopentasiloxane;

mixtures of two PDMSs with different viscosities, and more particularly of a PDMS gum and a PDMS oil, such as the product SF 1236 from the company General Electric. The product SF 1236 is a mixture of a gum SE 30 defined above, with a viscosity of 20 m$^2$/s, and of an oil SF 96 with a viscosity of $5\times10^{-6}$ m$^2$/s. This product preferably comprises 15% of gum SE 30 and 85% of an oil SF 96.

The organopolysiloxane resins that may be used in accordance with the invention are crosslinked siloxane systems containing the following units:

$R_2SiO_{2/2}$, $R_3SiO_{1/2}$, $RSiO_{3/2}$ and $SiO_{4/2}$ in which R represents an alkyl containing 1 to 16 carbon atoms. Among these products, those that are particularly preferred are those in which R denotes a $C_1$-$C_4$ lower alkyl group, more particularly methyl.

Mention may be made, among these resins, of the product sold under the name Dow Corning 593 or those sold under the names Silicone Fluid SS 4230 and SS 4267 by the company General Electric, which are silicones of dimethyl/trimethylsiloxane structure.

Mention may also be made of the resins of the trimethylsiloxysilicate type, sold in particular under the names X22-4914, X21-5034 and X21-5037 by the company Shin-Etsu.

The organomodified silicones that can be used in accordance with the invention are silicones as defined above and comprising in their structure one or more organofunctional groups attached via a hydrocarbon-based group.

In addition to the silicones described above, the organomodified silicones can be polydiarylsiloxanes, in particular polydiphenylsiloxanes, and polyalkylarylsiloxanes functionalized with the abovementioned organofunctional groups.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ m²/s at 25° C.

Mention may be made, among these polyalkylarylsiloxanes, by way of example, of the products sold under the following names:
- the Silbione® oils of the 70 641 series from Rhodia;
- the oils of the Rhodorsil® 70 633 and 763 series from Rhodia;
- the oil Dow Corning 556 Cosmetic Grade Fluid from Dow Corning;
- the silicones of the PK series from Bayer, such as the product PK20;
- the silicones of the PN and PH series from Bayer, such as the products PN1000 and PH1000;
- certain oils of the SF series from General Electric, such as SF 1023, SF 1154, SF 1250 and SF 1265.

Mention may be made, among the organomodified silicones, of polyorganosiloxanes comprising:
- substituted or unsubstituted amino groups, such as the products sold under the name GP 4 Silicone Fluid and GP 7100 by the company Genesee or the products sold under the names Q2 8220 and Dow Corning 929 or 939 by the company Dow Corning. The substituted amino groups are, in particular, $C_1$-$C_4$ aminoalkyl groups;
- alkoxylated groups, such as the product sold under the name Silicone Copolymer F-755 by SWS Silicones, and Abil Wax® 2428, 2434 and 2440 by the company Goldschmidt.

More particularly, the fatty substances are chosen from compounds that are liquid or pasty at ambient temperature (25° C.) and at atmospheric pressure.

Preferably, the fatty substance is a compound that is liquid at a temperature of 25° C. and at atmospheric pressure.

The fatty substances are advantageously chosen from $C_6$-$C_{16}$ alkanes, non-silicone oils of plant, mineral or synthetic origin, fatty alcohols, fatty acid and/or fatty alcohol esters, or mixtures thereof.

Preferably, the fatty substance is chosen from liquid petroleum jelly, $C_6$-$C_{16}$ alkanes, polydecenes, liquid fatty acid and/or fatty alcohol esters, liquid fatty alcohols, or mixtures thereof.

The composition according to the invention comprises at least 10% by weight of fatty substance, relative to the total weight of the composition, advantageously at least 15% by weight, even more advantageously at least 20% by weight, relative to the total weight of the composition, preferably at least 25% by weight, even more particularly at least 30% by weight and up to 70% by weight, relative to the total weight of the composition.

Cationic Polymer

As previously indicated, the composition comprises at least one cationic polymer.

It is recalled that, for the purposes of the present invention, the term "cationic polymer" denotes any polymer containing cationic groups and/or groups that can be ionized into cationic groups.

Preferably, the cationic polymer present in the composition according to the invention is a linear, random, graft or block homopolymer or copolymer and comprises at least one cationic group and/or group that can be ionized into a cationic group chosen from primary, secondary, tertiary and/or quaternary amine groups that form part of the main polymer chain or that are borne by a side substituent directly connected thereto.

Preferably, the cationic charge density of the cationic polymers according to the invention is greater than 1 meq/g and even more particularly greater than or equal to 4 meq/g.

This charge density is determined by the Kjeldahl method. It may also be calculated from the chemical nature of the polymer.

The cationic polymers used generally have a number-average molecular weight of between 500 and $5 \times 10^6$ approximately and preferably between $10^3$ and $3 \times 10^6$ approximately.

Among the cationic polymers, mention may more particularly be made of polymers of the polyamine, polyaminoamide and polyquaternary ammonium type.

These are known products and are especially described in patents FR 2505348 or FR 2542997.

Among the cationic polymers that may be used in the context of the invention, mention may be made of the following polymers, alone or as a mixture:

(1) Homopolymers or copolymers derived from acrylic or methacrylic esters or amides and comprising at least one of the units of formula (I), (II), (III) or (IV) below:

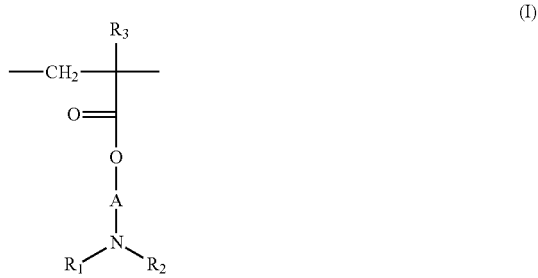

(I)

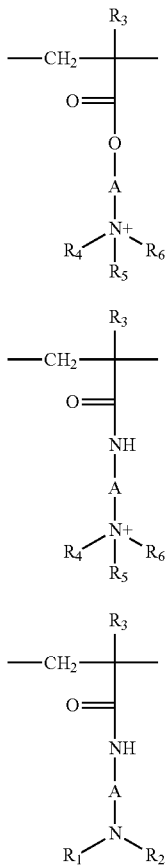

in which:
R₃, which may be identical or different, denote a hydrogen atom or a CH₃ radical;
A, which may be identical or different, represent a linear or branched $C_1$-$C_6$ and preferably $C_2$-$C_3$ alkyl group or a $C_1$-$C_4$ hydroxyalkyl group;
R₄, R₅ and R₆, which may be identical or different, represent a $C_1$-$C_{18}$ alkyl group or a benzyl radical, and preferably a $C_1$-$C_6$ alkyl group;
R₁ and R₂, which may be identical or different, represent hydrogen or a $C_1$-$C_6$ alkyl group, and preferably methyl or ethyl;
X denotes an anion derived from a inorganic or organic acid, such as a methosulfate anion or a halide such as chloride or bromide.

The polymers of family (1) can also contain one or more units derived from comonomers which may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Thus, among these polymers of family (1), mention may be made of:
  copolymers of acrylamide and of dimethylaminoethyl methacrylate quaternized with dimethyl sulfate or with a dimethyl halide, such as the product sold under the name Hercofloc by the company Hercules,
  the copolymers of acrylamide and of methacryloyloxy-ethyl-trimethylammonium chloride described, for example, in EP 80 976 and sold under the name Bina Quat P 100 by the company Ciba Geigy,
  the copolymer of acrylamide and of methacryloyloxyethyltrimethylammonium methosulfate sold under the name Reten by the company Hercules,
  quaternized or non-quaternized vinylpyrrolidone/dialkylaminoalkyl acrylate or methacrylate copolymers, such as the products sold under the name Gafquat by the company ISP, for instance Gafquat 734 or Gafquat 755, or alternatively the products known as Copolymer 845, 958 and 937. These polymers are described in FR 2 077 143 and FR 2 393 573,
  dimethylaminoethyl methacrylate/vinylcaprolactam/vinylpyrrolidone terpolymers, such as the product sold under the name Gaffix VC 713 by the company ISP,
  vinylpyrrolidone/methacrylamidopropyldimethylamine copolymers sold in particular under the name Styleze CC 10 by ISP,
  quaternized vinylpyrrolidone/dimethylaminopropylmethacrylamide copolymers such as the product sold under the name Gafquat HS 100 by the company ISP, and
  the crosslinked polymers of methacryloyloxy($C_1$-$C_4$) alkyl tri($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with an olefinically unsaturated compound, more particularly methylenebisacrylamide. Use may more particularly be made of a crosslinked acrylamide/methacryloyloxyethyltrimethylammonium chloride copolymer (20/80 by weight) in the form of a dispersion containing 50% by weight of said copolymer in mineral oil. This dispersion is sold under the name Salcare® SC 92 by the company Ciba. Use may also be made of a crosslinked homopolymer of methacryloyloxyethyltrimethylammonium chloride containing approximately 50% by weight of the homopolymer in mineral oil or in a liquid ester. These dispersions are sold under the names Salcare® SC 95 and Salcare® SC 96 by the company Ciba.

(2) Cationic cellulose derivatives such as cellulose copolymers or cellulose derivatives grafted with a water-soluble quaternary ammonium monomer, and disclosed in particular in U.S. Pat. No. 4,131,576, such as hydroxyalkyl celluloses, for instance hydroxymethyl, hydroxyethyl or hydroxypropyl celluloses grafted in particular with a methacryloylethyltrimethylammonium, methacrylamidopropyltrimethylammonium or dimethyldiallylammonium salt.

The commercial products corresponding to this definition are more particularly the products sold under the names Celquat L 200 and Celquat H 100 by the company National Starch.

(3) Cationic guar gums described more particularly in U.S. Pat. No. 3,589,578 and U.S. Pat. No. 4,031,307, such as guar gums containing cationic trialkylammonium groups. Use is made, for example, of guar gums modified with a 2,3-epoxypropyltrimethylammonium salt (for example, chloride).

Such products are sold especially under the trade names Jaguar C135, Jaguar C15, Jaguar C17 and Jaguar C162 by the company Meyhall.

(4) Polymers consisting of piperazinyl units and of divalent alkylene or hydroxyalkylene radicals containing straight or branched chains, optionally interrupted with oxygen, sulfur or nitrogen atoms or with aromatic or heterocyclic rings, and also the oxidation and/or quaternization products of these polymers. Such polymers are described, in particular, in FR 2 162 025 and FR 2 280 361.

(5) Water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyaminoamide; these polyaminoamides may be alkylated or, if they contain one or more tertiary amine functions, they may be quaternized. Such polymers are described, in particular, in FR 2 252 840 and FR 2 368 508.

Polyaminoamide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical is $C_1$-$C_4$ and preferably denotes methyl, ethyl or propyl. Such polymers are described in particular in FR 1 583 363.

Among these derivatives, mention may be made more particularly of the adipic acid/dimethylaminohydroxypropyl/diethylenetriamine polymers sold under the name Cartaretine F, F4 or F8 by the company Sandoz.

(6) Polymers obtained by reaction of a polyalkylene polyamine containing two primary amine groups and at least one secondary amine group with a dicarboxylic acid chosen from diglycolic acid and saturated $C_3$-$C_8$ aliphatic dicarboxylic acids. The mole ratio of the polyalkylene polyamine to the dicarboxylic acid is between 0.8:1 and 1.4:1; the polyaminoamide resulting therefrom being reacted with epichlorohydrin in a mole ratio of epichlorohydrin relative to the secondary amine group of the polyaminoamide of between 0.5: 1 and 1.8: 1. Such polymers are described in particular in U.S. Pat. No. 3,227,615 and U.S. Pat. No. 2,961,347.

Polymers of this type are sold in particular under the name Hercosett 57, PD 170 or Delsette 101 by the company Hercules.

(7) Cyclopolymers of alkyldiallylamine or of dialkyldiallylammonium, such as the homopolymers or copolymers containing, as main constituent of the chain, units corresponding to formula (V) or (VI):

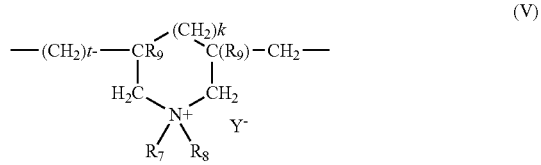

(V)

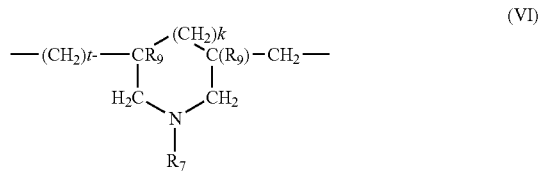

(VI)

in which formulae k and t are equal to 0 or 1, the sum k+t being equal to 1; $R_9$ denotes a hydrogen atom or a methyl radical; $R_7$ and $R_8$, independently of one another, denote a $C_1$-$C_8$ alkyl group, a hydroxyalkyl group in which the alkyl group is $C_1$-$C_5$, an amidoalkyl group in which the alkyl is $C_1$-$C_4$; $R_7$ and $R_8$ can also denote, together with the nitrogen atom to which they are attached, a heterocyclic group such as piperidyl or morpholinyl; $R_7$ and $R_8$, independently of one another, preferably denote a $C_1$-$C_4$ alkyl group; $Y^-$ is an organic or inorganic anion such as bromide, chloride, acetate, borate, citrate, tartrate, bisulfate, bisulfite, sulfate or phosphate. These polymers are described in particular in FR 2 080 759 and FR 2 190 406.

The cyclopolymers preferably comprise at least one unit of formula (V).

As regards the copolymers, they also comprise an acrylamide monomer.

Among the polymers defined above, mention may be made more particularly of the dimethyldiallylammonium chloride homopolymer sold under the name Merquat 100 by the company Nalco (and its homologues of low weight-average molecular mass) and the copolymers of diallyldimethylammonium chloride and of acrylamide, sold under the name Merquat 550.

(8) The diquaternary ammonium polymer containing repeating units corresponding to the formula:

(VII)

in which formula:

$R_{10}$, $R_{11}$, $R_{12}$ and $R_{13}$, which may be identical or different, represent $C_1$-$C_{20}$ aliphatic, alicyclic or arylaliphatic radicals or hydroxyalkylaliphatic radicals in which the alkyl radical is $C_1$-$C_4$, or alternatively $R_{10}$, $R_{11}$, $R_{12}$ and $R_{13}$, together or separately, constitute, with the nitrogen atoms to which they are attached, heterocycles optionally containing a second heteroatom other than nitrogen, or alternatively $R_{10}$, $R_{11}$, $R_{12}$ and $R_{13}$ represent a linear or branched $C_1$-$C_6$ alkyl radical substituted with a nitrile, ester, acyl or amide group or a group —CO—O—$R_{14}$-D or —CO—NH—$R_{14}$-D where $R_{14}$ is an alkylene and D is a quaternary ammonium group;

$A_1$ and $B_1$ represent $C_2$-$C_{20}$ polymethylene groups which may be linear or branched, and saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from an inorganic or organic acid;

$A_1$, $R_{10}$ and $R_{12}$ can form, with the two nitrogen atoms to which they are attached, a piperazine ring;

in addition, if $A_1$ denotes a linear or branched, saturated or unsaturated alkylene or hydroxyalkylene radical, $B_1$ can also denote a —$(CH_2)_n$—CO-D-OC—$(CH_2)_n$— group in which n is between 1 and 100 and preferably between 1 and 50, and D denotes:

a) a glycol residue of formula: —O—Z—O—, where Z denotes a linear or branched hydrocarbon-based radical or a group corresponding to one of the following formulae:

—(CH$_2$—CH$_2$—O)$_x$—CH$_2$—CH2-; —[CH$_2$—CH(CH$_3$)—O]$_y$—CH$_2$—CH(CH$_3$)—, where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon-based radical, or alternatively the radical —CH$_2$—CH$_2$—S—S—CH$_2$—CH$_2$;

d) a ureylene group of formula: —NH—CO—NH—.

Preferably, X$^-$ is an anion such as chloride or bromide.

These polymers generally have a number-average molecular weight of between 1000 and 100 000.

Polymers of this type are described in particular in FR 2 320 330, FR 2 270 846, FR 2 316 271, FR 2 336 434, FR 2 413 907, U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that consist of repeating units corresponding to the following formula (VIII):

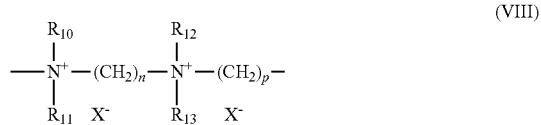

in which R$_{10}$, R$_{11}$, R$_{12}$ and R$_{13}$, which may be identical or different, denote a C$_1$-C$_4$ alkyl or hydroxyalkyl radical, n and p are integers ranging from 2 to 20 approximately, and X$^-$ is an anion derived from an inorganic or organic acid.

(9) Polyquaternary ammonium polymers consisting of repeating units of formula (IX):

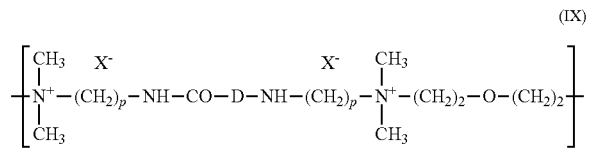

in which p denotes an integer ranging from 1 to 6 approximately, D may be zero or may represent a —(CH$_2$)$_r$—CO— group in which r denotes a number equal to 4 or 7, and X$^-$ is an anion;

Such polymers may be prepared according to the processes described in U.S. Pat. Nos. 4,157,388, 4,702,906 and 4,719,282. They are especially described in patent application EP 122 324.

Among these polymers, examples that may be mentioned include the products Mirapol A 15, Mirapol AD1, Mirapol AZ1 and Mirapol 175 sold by the company Miranol.

(10) Quaternary polymers of vinylpyrrolidone and of vinylimidazole, for instance the products sold under the names Luviquat FC 905, FC 550 and FC 370 by the company BASF.

(11) Polyamines such as Polyquart H sold by Cognis, referred to under the name polyethylene glycol (15) tallow polyamine in the CTFA dictionary.

Other cationic polymers that may be used in the context of the invention are polyalkyleneimines, in particular polyethyleneimines, polymers containing vinylpyridine or vinylpyridinium units, condensates of polyamines and of epichlorohydrin, polyquaternary ureylenes and chitin derivatives.

Among all the cationic polymers that may be used in the context of the present invention, it is preferred to use, alone or as mixtures, polymers of families (1), (7), (8) and (9). In accordance with one more particular embodiment of the invention, it is preferred to use polymers of families (7), (8) and (9).

According to an even more advantageous embodiment of the invention, use is made of polymers of families (7) and (8), alone or as mixtures, and more preferentially still of polymers having repeating units of formulae (W) and (U) below:

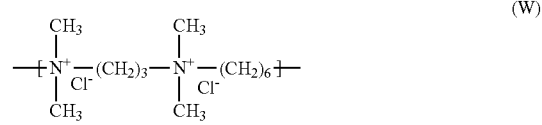

and in particular those of which the molecular weight, determined by gel permeation chromatography, is between 9500 and 9900;

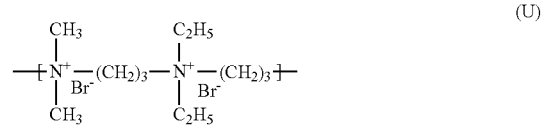

and in particular those of which the molecular weight, determined by gel permeation chromatography, is about 1200.

Generally, the content of cationic polymer(s) represents from 0.01% to 10% by weight, more particularly from 0.05% to 6% by weight, and even more preferentially between 0.1% and 5% by weight, relative to the weight of the composition.

Non-Ionic Guar Gum

In accordance with one particularly advantageous embodiment of the invention, the composition comprises at least one non-ionic guar gum.

The term "non-ionic guar gum" is intended to mean unmodified non-ionic guar gums and modified non-ionic guar gums.

The unmodified non-ionic guar gums are, for example, the products sold under the name Vidogum GH 175 by the company Unipectine and under the names Meypro-Guar 50 and Jaguar C by the company Rhodia Chimie.

The modified non-ionic guar gums are in particular modified with C$_1$-C$_6$ hydroxyalkyl groups.

Among the hydroxyalkyl groups that may be mentioned, for example, are hydroxymethyl, hydroxyethyl, hydroxypropyl and hydroxybutyl groups.

These hydroxyalkylated guar gums are well known in the prior art and can be prepared, for example, by reacting corresponding alkene oxides such as, for example, propylene oxides, with the guar gum so as to obtain a guar gum modified with hydroxypropyl groups.

The degree of hydroxyalkylation, which corresponds to the number of alkylene oxide molecules consumed by the number of free hydroxyl functions present on the guar gum, preferably ranges from 0.4 to 1.2.

Such non-ionic guar gums optionally modified with hydroxyalkyl groups are sold, for example, under the trade names Jaguar HP8, Jaguar HP60 and Jaguar HP120, Jaguar DC 293 and Jaguar HP 105 by the company Rhodia Chimie or under the name Galactasol 4H4FD2 by the company Aqualon.

Also suitable are non-ionic guar gums modified with hydroxyalkyl groups, more especially hydroxypropyl groups, modified with groups comprising at least one $C_6$-$C_{30}$ fatty chain. By way of example of such compounds, mention may be made, inter alia, of the product Esaflor HM 22® ($C_{22}$ alkyl chain) sold by the company Lamberti, and the products RE210-18® ($C_{14}$ alkyl chain) and RE205-1® ($C_{20}$ alkyl chain) sold by the company Rhône-Poulenc.

More particularly, the content of non-ionic guar gum(s), if this or these compound(s) is or are present, ranges from 0.001% to 10% by weight, preferably from 0.01% to 5% by weight, relative to the total weight of the composition.

Alkaline Agent

The composition according to the invention may optionally comprise according to one particularly advantageous embodiment of the invention, at least one alkaline agent.

This agent may be chosen from inorganic or organic or hybrid alkaline agents, or mixtures thereof.

The inorganic alkaline agent(s) are preferably chosen from aqueous ammonia, alkali carbonates or bicarbonates such as sodium or potassium carbonates and sodium or potassium bicarbonates, sodium hydroxide or potassium hydroxide, or mixtures thereof.

The organic alkaline agent(s) are preferably chosen from organic amines with a pKb at 25° C. of less than 12, preferably less than 10 and even more advantageously less than 6. It should be noted that it is the pKb corresponding to the function of highest basicity.

Mention may be made, as hybrid compounds, of the salts of the abovementioned amines with acids, such as carbonic acid or hydrochloric acid.

The organic alkaline agent(s) are chosen, for example, from alkanolamines, oxyethylenated and/or oxypropylenated ethylenediamines, amino acids and the compounds having the formula below:

$$\begin{array}{c} Rx \\ \diagdown \\ N-W-N \\ \diagup \\ Ry \end{array} \begin{array}{c} Rz \\ \diagup \\ \\ \diagdown \\ Rt \end{array}$$

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Alkanolamines such as monoalkanolamines, dialkanolamines or trialkanolamines comprising from one to three identical or different $C_1$-$C_4$ hydroxyalkyl radicals are in particular suitable for implementing the invention.

Among compounds of this type, mention may be made of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in their L, D or racemic form, and comprise at least one acid function chosen more particularly from carboxylic acid, sulfonic acid, phosphonic acid or phosphoric acid functions. The amino acids can be in the neutral or ionic form.

Mention may in particular be made, as amino acids which can be used in the present invention, of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to the formula below:

$$R-CH_2-CH\begin{array}{c} NH_2 \\ \diagup \\ \\ \diagdown \\ CO_2H \end{array}$$

in which R denotes a group chosen from:

$$\begin{array}{c} \text{imidazole ring} \\ NH \end{array} \quad -(CH_2)_3NH_2$$

$$-(CH_2)_2NH_2 \quad -(CH_2)_2NHCONH_2$$

$$-(CH_2)_2NH-\underset{\underset{NH}{\|}}{C}-NH_2$$

The compounds corresponding to the formula above are histidine, lysine, arginine, ornithine and citrulline.

The organic amine may also be chosen from organic amines of heterocyclic type. Besides histidine that has already been mentioned in the amino acids, mention may be made in particular of pyridine, piperidine, imidazole, triazole, tetrazole and benzimidazole.

The organic amine can also be chosen from amino acid dipeptides. As amino acid dipeptides that may be used in the present invention, mention may be made especially of carnosine, anserine and balenine.

The organic amine is chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

As hybrid compounds, mention may be made in particular of guanidine carbonate or monoethanolamine hydrochloride.

According to one embodiment of the invention, the dye composition used in the process of the invention contains, as alkaline agent, aqueous ammonia and/or at least one alkanolamine and/or at least one basic amino acid, more advantageously aqueous ammonia and/or at least one alkanolamine.

Preferably, the alkaline agent is chosen from aqueous ammonia and monoethanolamine, or mixtures thereof.

Even more preferentially, the alkaline agent is an alkanolamine and better still is monoethanolamine.

Advantageously, the composition has a content of alkaline agent(s), and preferably of organic amine(s), when it (they) is (are) present, ranging from 0.01% to 30% by weight, preferably from 0.1% to 20% by weight and better still from 1% to 10% by weight, relative to the weight of said composition. It should be noted that this content is expressed as $NH_3$ when the alkaline agent is aqueous ammonia.

Oxidizing Agent

The composition according to the invention also comprises at least one oxidizing agent.

It should be noted that the oxidizing agents present in the composition are different from atmospheric oxygen.

In particular, the oxidizing agent(s) suitable for the present invention are for example chosen from hydrogen peroxide, urea peroxide, alkali metal bromates or ferricyanides, peroxygenated salts, for instance persulfates, perborates, peracids and precursors thereof and percarbonates of alkali metals or alkaline-earth metals. Advantageously, the oxidizing agent is hydrogen peroxide.

The oxidizing agent(s) generally represent(s) from 0.1% to 50% by weight and preferably from 1% to 20% by weight relative to the total weight of the composition according to the invention.

Additives

The composition may also contain various adjuvants conventionally used in compositions for dyeing or lightening the hair, such as anionic, amphoteric or non-ionic polymers, or mixtures thereof; cationic surfactants; antioxidants; penetrants; sequestrants; fragrances; dispersants; film-forming agents; ceramides; preservatives; opacifiers, vitamins.

The above adjuvants are generally present in an amount, for each of them, of between 0.01% and 20% by weight relative to the weight of the composition.

In a specific embodiment, the composition of the invention contains at least one vitamin.

The vitamins that may be of use in the composition of the invention can in particular be chosen from vitamin C, A vitamins, B vitamins, D vitamins, vitamin E and vitamin F, and derivatives thereof.

Vitamin C

Vitamin C corresponds to ascorbic acid which is generally in L form, since it is usually extracted from natural products. Ascorbic acid derivatives are, more particularly, its salts, such as in particular sodium ascorbate, magnesium ascorbyl phosphate or sodium ascorbyl phosphate; it esters, for instance in particular its esters such as ascorbyl acetate, ascorbyl palmitate and ascorbyl propionate; its oxidized form, dehydroascorbic acid; or its sugars, such as in particular glycosylated ascorbic acid, and mixtures thereof.

Vitamin B3

Vitamin B3, also known as vitamin PP, is a compound of formula

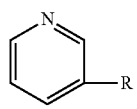

in which R can be —$CONH_2$ (niacinamide), —COOH (nicotinic acid or niacin), or $CH_2OH$ (nicotinyl alcohol), —CO—NH—$CH_2$—COOH (nicotinuric acid) or —CO—NH—OH (niconityl hydroxamic acid).

As vitamin B3 derivatives, mention may, for example, be made of nicotinic acid esters such as tocopheryl nicotinate, amides derived from niacinamide by substitution of hydrogen groups of —$CONH_2$, products of reaction with carboxylic acids and amino acids, and esters of nicotinyl alcohol and of carboxylic acids such as acetic acid, salicylic acid, glycolic acid or palmitic acid. Mention may also be made of the following derivatives: 2-chloronicotinamide, 6-methylnicotinamide, 6-aminonicotinamide, N-methylnicotinamide, N,N-dimethylnicotinamide, N-(hydroxymethyl)nicotinamide, quinolinic acid imide, nicotinanilide, N-benzylnicotinamide, N-ethylnicotinamide, nifenazone, nicotinaldehyde, isonicotinic acid, methylisonicotinic acid, thionicotinamide, nialamide, 2-mercaptonicotinic acid, nicomol et niaprazine.

As other vitamin B3 derivatives, mention may also be made of its inorganic salts, such as chlorides, bromides, iodides or carbonates, and its organic salts, such as the salts obtained by reaction with carboxylic acids, such as acetate, salicylate, glycolate, lactate, malate, citrate, mandelate, tartrate, etc.

Vitamin B5

Vitamin B5 is Pantothenic Acid

As vitamin B5 derivatives, use may be made of panthenol or panthenyl alcohol or 2,4-dihydroxy-N-(3-hydroxypropyl)-3,3-dimethylbutanamide, in its various forms: D-panthenol, DL-panthenol which is the alcohol form of pantothenic acid and one of its precursors. Use may also be made, as derivatives, of calcium pantothenate, pantethine, pantotheine, panthenyl ethyl ether, pangamic acid, pyridoxine, pantoyl lactose, and natural compounds containing same, such as royal jelly.

Vitamin D

As vitamin D, mention may be made of vitamin D1(lumisterol(1)/calciferol(1) complex), vitamin D2 (calciferol) and vitamin D3 (colecalciferol). By way of derivatives, mention may be made of vitamin D analogues such as those described in document WO-A-00/26167, for instance:

3-hydroxymethyl-5-{2-[3-(5-hydroxy-5- or 6-methylhexyl)phenyl]vinyl}phenol,
3-[3-(5-hydroxy-1,5-(dimethyphexyl)phenoxymethyl]-5-hydroxymethylphenol,
6-[3-(3,4-bis(hydroxymethyl)benzyloxy)phenyl]-2-methyl-hepta-3,5-dien-2-ol,
6-[3-(3,4-bis(hydroxymethyl)benzyloxy)phenyl]-2-methyl-hexan-2-ol,
6-[3-(3,4-bis(hydroxymethyl)phenoxymethyl)phenyl]-2-methylheptan-2-ol,
7-[3-(3,4-bis(hydroxymethyl)phenoxymethyl)phenyl]-3-ethyloctan-3-ol,
5-{2-[4-(5-hydroxy-5-methylhexyl)phenyl]-vinylou-ethyl}benzene-1,3-diol,
5-{2-[3- or 4-(6-hydroxy-6-methylheptyl)phenyl]vinyl}benzene-1,3-diol,
5-{2-[3- or 4-(6-hydroxy-6-methylheptyl)phenyl]ethyl}benzene-1,3-diol,
2-hydroxymethyl-4-{2-[3- or 4-(5-hydroxy-5-methylhexyl)phenyl]vinyl}phenol,
2-hydroxymethyl-4-{2-[3 or 4-(6-hydroxy-6-methylheptyl)phenyl]vinyl}phenol,
2-hydroxymethyl-4-{2-[3- or 4-(5-hydroxy-5-methylheptyl)phenyl]ethyl}phenol,
2-hydroxymethyl-4-{2-[3- or 4-(6-hydroxy-6-methylheptyl)phenyl]ethyl}phenol, 2-hydroxymethyl-5-{2-[4-(5-hydroxy-5-methylhexyl)phenyl]vinyl}phenol,
6-[3-(3,4-bis(hydroxymethyl)benzyloxy)phenyl]-2-methylheptan-2-ol,
4-[3-(5-hydroxy-1,5-(dimethyphexyl)phenoxymethyl]-2-hydroxymethylphenol,
6-{3- or 4-[2-(3,4-bis(hydroxymethyl)phenyl)vinyl]phenyl}-2-methylhexan-2-ol,
7-{4-[2-(3,4-bis(hydroxymethyl)phenyl)vinyl]phenyl}-2-methylheptan-2-ol,
5-{2-[3-(6-hydroxy-6-methylheptyl)phenyl]-1-methylvinyl}benzene-1,3-diol,
5-{2-[3-(5-hydroxy-5-methylhexyl)phenyl]vinyl}benzene-1,3-diol,
5-[3-(6-hydroxy-6-methylheptyl)phenoxymethyl]benzene-1,3-diol,
5-{2-[3-(7-hydroxy-7-methyloct-1-enyl)phenyl]vinyl}benzene-1,3-diol,
5-{2-[3-(7-hydroxy-7-methyloctyl)phenyl]vinyl}benzene-1,3-diol,
4-{2-[3-(6-hydroxy-6-methylheptyl)phenyl]vinyl}benzene-1,2-diol,
3-{2-[3-(6-hydroxy-6-methylheptyl)phenyl]vinyl}phenol,
6-{3-[2-(3,5-bis(hydroxymethyl)phenyl)vinyl]phenyl}-2-methylhexan-2-ol,
3-{2-[3-(7-hydroxy-7-methyloctyl)phenyl]vinyl}phenol,
7-{3-[2-(3,5-bis(hydroxymethyl)phenyl)vinyl]phenyl}-2-methylheptan-2-ol,
7-{3-[2-(3,4-bis(hydroxymethyl)phenyl)vinyl]phenyl}-2-methylheptan-2-ol,
7-{3-[2-(4-hydroxymethylphenyl)vinyl]phenyl}-2-methylheptan-2-ol,
4-{2-[3-(7-hydroxy-7-methyloct-1-enyl)phenyl]vinyl}benzene-1,2-diol,
7-[3-(3,4-bis(hydroxymethyl)phenylethynyl)phenyl]-2-methylheptan-2-ol,
5-{2-[3-(6-hydroxy-6-methylhept-1-enyl)phenyl]vinyl}benzene-1,3-diol,
5-{2-[3-(7-ethyl-7-hydroxynon-1-enyl)phenyl]vinyl}benzene-1,3-diol,
5-{2-[3-(7-hydroxy-1-methoxy-1,7-dimethyloctyl)phenyl]vinyl}benzene-1,3-diol,
5-{2-[3-(6-hydroxy-1-methoxy-1,6-dimethylheptyl)phenyl]vinyl}benzene-1,3-diol,
5-{2-[3-(5-hydroxypentyl)phenyl]vinyl}benzene-1,3-diol,
5-{2-[3-(5-hydroxy-6-methylheptyl)phenyl]vinyl}benzene-1,3-diol,
5-{2-[3-(6-hydroxy-7-methyloctyl)phenyl]vinyl}benzene-1,3-diol,
5-{2-[3-(5-hydroxy-6-methylhept-1-enyl)phenyl]vinyl}benzene-1,3-diol,
5-{2-[3-(6-hydroxy-7-methyloct-1-enyl)phenyl]vinyl}benzene-1,3-diol,
5-{2-[3-(1,6-dihydroxy-1,6-dimethylheptyl)phenyl]vinyl}benzene-1,3-diol,
5-{2-[3-(6-hydroxy-1,6-(dimethyl)hept-1-enyl)phenyl]vinyl}benzene-1,3-diol.

Vitamin F

Vitamin F is a mixture of essential fatty acids, i.e. of unsaturated acids which have at least one double bond, such as linoleic acid or 9,12-octadecadienoic acid and its stereoisomers, linolenic acid in a form (9,12,15-octadecatrienoic acid) or γ form (6,9,12-octadecatrienoic acid) and their stereoisomers, arachidonic acid or 5,8,11,14-eicosatetraenoic acid and its stereoisomers.

Vitamin F, or mixtures of unsaturated acids which have at least one double bond and in particular mixtures of linoleic acid, linolenic acid and arachidonic acid, or the compounds containing same, and in particular oils of vegetable origin containing same, for instance jojoba oil, can be used in the composition of the present invention.

Vitamin E

Vitamin E is alpha-tocopherol.

The vitamin E derivatives can be chosen from esters of vitamin E, and in particular the acetate, succinate or nicotinate.

The composition of the invention can comprise one or more vitamins, of the same category or of different categories.

Preferably, the vitamins are chosen from water-soluble vitamins and in particular vitamins B or C.

According to one particular embodiment, the composition comprises at least vitamin C in ascorbic acid form.

The vitamin(s) may be present in an amount ranging from 0.005% to 1% by weight, and preferably from 0.1% to 1% by weight, of active material relative to the total weight of the composition.

The composition according to the invention may comprise water and/or one or more organic solvents.

Examples of organic solvents that may be mentioned include linear or branched and preferably saturated monoalcohols or diols, comprising 2 to 10 carbon atoms, such as ethyl alcohol, isopropyl alcohol, hexylene glycol (2-methyl-2,4-pentanediol), neopentyl glycol and 3-methyl-1,5-pentanediol, butylene glycol, dipropylene glycol and propylene glycol; aromatic alcohols such as benzyl alcohol or phenylethyl alcohol; polyols containing more than two hydroxyl functions, such as glycerol; polyol ethers, for instance ethylene glycol monomethyl, monoethyl or monobutyl ether, propylene glycol or ethers thereof, for instance propylene glycol monomethyl ether; and also diethylene glycol alkyl ethers, especially $C_1$-$C_4$ alkyl ethers, for instance diethylene glycol monoethyl ether or monobutyl ether, alone or as a mixture.

The organic solvents, when they are present, generally represent between 1% and 40% by weight relative to the total weight of the dye composition, and preferably between 5% and 30% by weight relative to the total weight of the dye composition.

The composition is preferably aqueous.

In this case, it preferably comprises from 30% to 95% by weight of water, better still from 40% to 90% by weight of water and even better still from 50% to 85% by weight of water relative to the total weight of the composition.

The pH of the composition according to the invention, if it is aqueous, generally ranges from 6 to 11 and preferentially from 8.5 to 11.

It can be adjusted by adding acidifying agents, such as hydrochloric acid, (ortho)phosphoric acid, sulfuric acid, boric acid, and also carboxylic acids, for instance acetic acid, lactic acid or citric acid, or sulfonic acids. Alkaline agents such as those previously mentioned may also be used.

Dyeing Process

The composition described previously is applied to wet or dry keratin fibres.

It is usually left in place on the fibres for a time generally of from 1 minute to 1 hour and preferably from 5 minutes to 30 minutes.

The temperature during the dyeing process is conventionally between ambient temperature (between 15° C. and 25° C.) and 80° C. and preferably between ambient temperature and 60° C.

On conclusion of the treatment, the human keratin fibres are advantageously rinsed with water. They can optionally be washed with a shampoo, followed by rinsing with water, before being dried or left to dry.

The composition applied in the process according to the invention is generally prepared extemporaneously before the application, by mixing at least two formulations.

In particular, a formulation (A) free of oxidizing agent different from atmospheric oxygen and comprising colouring agent chosen from oxidation dye precursors, direct dyes and mixtures thereof; at least one anionic surfactant and a formulation (B) comprising at least one oxidizing agent different from atmospheric oxygen are mixed; both or either of the compositions comprising at least one fatty substance, at least one cationic polymer, at least one amphoteric or zwitterionic surfactant; at least one non-ionic surfactant; at least one anionic surfactant; the mixture obtained from formulations (A) and (B) comprising at least 10% by weight of fatty substance relative to the total weight of the composition (of the mixture).

Advantageously, formulation (A) comprises at least one amphoteric or zwitterionic surfactant; at least one non-ionic surfactant; at least one anionic surfactant.

Advantageously, formulations (A) and (B) are aqueous.

The term "aqueous formulation" is intended to mean a composition comprising at least 5% by weight of water, relative to the weight of this formulation.

Preferably, an aqueous formulation comprises more than 10% by weight of water and even more advantageously more than 20% by weight of water.

Preferably, formulation (A) comprises at least one fatty substance, preferably at a content of at least 50% by weight, and even more preferentially at least 50% by weight of fatty substances that are liquid at ambient temperature (25° C.), relative to the weight of this formulation (A).

Advantageously, formulation (A) is a direct emulsion (oil-in-water: O/W) or an inverse emulsion (water-in-oil: W/O), and preferably a direct emulsion (O/W).

More particularly, formulation (A) comprises at least one basifying agent.

As regards formulation (B) comprising the oxidizing agent as previously defined, it can also comprise one or more basifying agents as previously indicated.

Usually, the pH of the oxidizing composition, when it is aqueous, is less than 7.

Preferably, the oxidizing composition comprises hydrogen peroxide as oxidizing agent, in aqueous solution, the concentration of which varies, more particularly, from 0.1% to 50%, more particularly between 0.5% and 20% and even more preferentially between 1% and 15% by weight, relative to the weight of the oxidizing composition.

In accordance with one particular variant of the invention, the composition (B) comprises at least one fatty substance.

Preferably, in the case of this variant, the fatty substance content is at least 5% by weight, preferably at least 10% by weight, and more advantageously at least 15% of fatty substances that are liquid at ambient temperature (25° C.), relative to the weight of this formulation.

According to another advantageous variant of the invention, formulation (B) comprises at least one cationic polymer.

Moreover, formulations (A) and (B) are preferably mixed together before use, in an (A)/(B) weight ratio ranging from 0.2 to 10 and better still from 0.5 to 2.

In addition, the composition used in the process according to the invention, i.e. the composition resulting from mixing together the two formulations (A) and (B), has a fatty substance content of at least 10% by weight of fatty substance, relative to the weight of the composition resulting from mixing together the two abovementioned formulations.

Everything that has been described previously concerning the ingredients of the composition according to the invention remains valid in the case of formulations (A) and (B), the contents taking into account the degree of dilution during mixing.

The examples that follow serve to illustrate the invention without, however, being limiting in nature.

EXAMPLE

The following compositions are prepared (the amounts are expressed in g % of active material):

Composition 1:

| | |
|---|---|
| Resorcinol | 0.5 |
| Ethanolamine | 5 |
| Sodium laureth sulfate comprising 2 OE | 1.75 |
| Hydroxypropyl guar | 1 |
| Ascorbic acid | 0.5 |
| N,N-Bis(2-hydroxyethyl)-p-phenylenediamine sulfate | 0.073 |
| m-Aminophenol | 0.18 |
| EDTA | 0.2 |
| 2-Methylresorcinol | 0.1 |
| PEG-40 hydrogenated castor oil | 1 |
| 2,4-Diaminophenoxyethanol hydrochloride | 0.019 |
| Cocobetaine | 3 |
| Sodium chloride | 0.65 |
| Sodium metabisulfite | 0.5 |
| Mineral oil | 60 |
| 2,5-Toluenediamine | 0.6732 |
| Water | q.s. for 100 |

Composition 2:

| | |
|---|---|
| Tocopherol | 0.1 |
| Sodium stannate | 0.04 |
| Pentasodium pentetate | 0.06 |
| Polyquaternium-6 | 0.2 |
| Glycerol | 0.5 |
| Cetearyl alcohol | 6 |
| Hexadimethrine chloride | 0.15 |
| Hydrogen peroxide | 6 |
| Tetrasodium pyrophosphate | 0.03 |
| Mineral oil | 20 |
| PEG-4 Rapeseedamide | 1.19 |
| Steareth-20 | 5 |
| Phosphoric acid | q.s. for pH 2.2 |
| Water | q.s. for 100 |

Application Method:

The two compositions are mixed together at the time of use in the following proportions: 10 g of composition 1 with 15 g of composition 2.

The resulting mixture is easily applied to locks of dark chestnut hair in a proportion of 10 g of mixture for 1 g of hair, for 30 minutes at ambient temperature (20° C.).

The hair is then easily rinsed, then washed with a standard shampoo and dried.

A light chestnut colour is obtained.

Composition 3:

| | |
|---|---|
| Ethanolamine | 5 |
| Sodium laureth sulfate comprising 2.2 OE | 1.75 |
| Hydroxypropyl guar | 1 |
| Ascorbic acid | 0.5 |
| N,N-bis(2-Hydroxyethyl)-p-phenylenediamine sulphate | 0.073 |

-continued

| | |
|---|---|
| EDTA | 0.2 |
| PEG-40 hydrogenated castor oil | 1 |
| Cocobetaine | 3 |
| Sodium chloride | 0.65 |
| Sodium metabisulfite | 0.5 |
| Basic Yellow 87 | 0.3 |
| Basic Orange 31 | 0.225 |
| Mineral oil | 60 |
| Water | q.s. for 100 |

Composition 4:

| | |
|---|---|
| Tocopherol | 0.1 |
| Sodium stannate | 0.04 |
| Pentasodium pentetate | 0.06 |
| Polyquaternium-6 | 0.2 |
| Glycerol | 0.5 |
| Cetearyl alcohol | 6 |
| Hexadimethrine chloride | 0.15 |
| Hydrogen peroxide | 6 |
| Tetrasodium pyrophosphate | 0.03 |
| Mineral oil | 20 |
| PEG-4 Rapeseedamide | 1.19 |
| Steareth-20 | 5 |
| Phosphoric acid | q.s. for pH 2.2 |
| Water | q.s. for 100 |

Application Method:

The two compositions are mixed at the time of use in the following proportions: 10 g of composition 3 with 15 g of composition 4.

The resulting mixture is easily applied to locks of dark chestnut hair in a proportion of 10 g of mixture for 1 g of hair, for 30 minutes at ambient temperature (20° C.).

The hair is then easily rinsed, then washed with a standard shampoo and dried.

A coppery light chestnut colour is obtained.

The invention claimed is:

1. A composition for dyeing keratin fibers, comprising:
at least one coloring agent chosen from oxidation dye precursors, direct dyes, or mixtures thereof;
at least one amphoteric or zwitterionic surfactant;
at least one non-ionic surfactant;
at least one anionic surfactant;
at least one fatty substance chosen from liquid paraffins, petroleum jelly, liquid petroleum jelly, polydecenes, or hydrogenated polyisobutene, present in an amount of at least 10% by weight, relative to the weight of the composition;
at least one cationic polymer; and
at least one oxidizing agent other than atmospheric oxygen
wherein the amphoteric surfactant and anionic surfactant are present in a weight ratio ranging from 0.1 to 10.

2. The composition according to claim 1, wherein at least one coloring agent is an oxidation dye precursor, chosen from oxidation bases or addition salts thereof.

3. The composition according to claim 2, wherein the oxidation dye precursors are chosen from couplers and acid addition salts thereof.

4. The composition according to claim 1, wherein the at least one coloring agent is a direct dye chosen from cationic direct dyes; azo direct dyes; (poly)methin dyes; carbonyl dyes; azine dyes; nitro (hetero)aryl dyes; tri(hetero)arylmethane dyes; porphyrins; phthalocyanines, natural direct dyes, or mixtures thereof.

5. The composition according to claim 1, wherein at least one coloring agent is chosen from direct dyes chosen from hydrazono cationic dyes of formulae (II) or (III), or azo cationic dyes of formulae (IV) or (V) below:

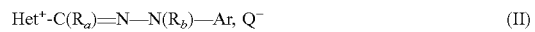  (II)

  (III)

  (IV)

  (V)

wherein:
Her$^+$ is a cationic heteroaryl radical, optionally substituted;
Ar$^+$ is an aryl radical carrying an exocyclic cationic charge;
Ar is chosen from an aryl group, optionally substituted, or a julolidine group;
Ar" is a (hetero)aryl group, optionally substituted;
$R_a$ and $R_b$, which may be identical or different, are chosen from a hydrogen atom or a ($C_1$-$C_8$)alkyl group which is optionally substituted; or $R_a$ with a substituent of Her$^+$ and/or $R_b$, with a substituent of Ar, form, together with the atoms which bear them, a (hetero)cycloalkyl; and
Q$^-$ is an organic or inorganic anionic counterion;
wherein the cationic direct dyes of formula (II) to (V) optionally carry endocyclic cationic charges.

6. A composition according to claim 1, wherein the at least one amphoteric or zwitterionic surfactant is chosen from derivatives of optionally quaternized aliphatic secondary or tertiary amines, in which derivatives the aliphatic group is a linear or branched chain comprising from 8 to 22 carbon atoms, said amine derivatives containing at least one anionic group.

7. The composition according to claim 1, wherein the at least one amphoteric or zwitterionic surfactant is chosen from the following compounds:
($C_8$-$C_{20}$)alkylbetaines,
($C_8$-$C_{20}$)alkylsulfobetaines,
($C_8$-$C_{20}$)alkylamido($C_3$-$C_8$)alkylbetaines,
($C_8$-$C_{20}$)alkylamido($C_6$-$C_8$)alkylsulfobetaines,
the compounds of following structure (B1):

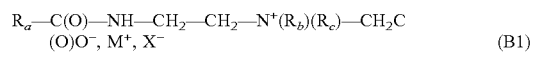  (B1)

wherein
$R_a$ represents a $C_{10}$-$C_{30}$ alkyl or alkenyl group derived from an acid $R_a$—COOH, or a heptyl, nonyl or undecyl group;
$R_b$ represents a β-hydroxyethyl group; and
$R_c$ represents a carboxymethyl group;
M$^+$ represents a cationic counterion derived from an alkali metal or alkaline-earth metal, an ammonium ion or an ion derived from an organic amine, and
X$^-$ represents an organic or inorganic anionic counterion, or alternatively M$^+$ and X$^-$ are absent,
the compounds of following structure (B2):

  (B2)

wherein
B is the group —$CH_2$—$CH_2$—O—X';
B' is the group —$(CH_2)_z$Y', with z equal to the integer 1 or 2;
X' is chosen from the groups —$CH_2$—C(O)OH, —$CH_2$—C(O)OZ', —$CH_2$—$CH_2$—C(O)OH, —$CH_2$—$CH_2$—C(O)OZ', or a hydrogen atom;

Y' is chosen from the groups —C(O)OH, —C(O)OZ', —CH$_2$—CH(OH)—SO$_3$H or —CH$_2$—CH(OH)—SO$_3$—Z';

Z' is chosen from cationic counterions derived from an alkali metal or alkaline-earth metal, an ammonium ion or an ion derived from an organic amine;

R$_{a'}$ is chosen from C$_{10}$-C$_{30}$ alkyl or alkenyl groups of an acid R$_{a'}$—C(O)OH, alkyl groups, or unsaturated C$_{17}$ groups, and the compounds of formula (B'2):

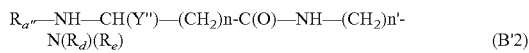

(B'2)

wherein:
Y" is chosen from the groups —C(O)OH, —C(O)OZ", —CH$_2$—CH(OH)—SO$_3$H or —CH$_2$—CH(OH)—SO$_3$—Z";

R$_d$ and R$_e$, independently of each other, are C$_1$-C$_4$ alkyl or hydroxyalkyl radicals;

Z" is chosen from cationic counterions derived from an alkali metal or alkaline-earth metal, an ammonium ion or an ion derived from an organic amine;

R$_{a''}$ is chosen from C$_{10}$-C$_{30}$ alkyl or alkenyl groups of an acid R$_{a''}$—C(O)OH; and n and n', independently of each other, are integers ranging from 1 to 3.

8. The composition according to claim 1, wherein the at least one amphoteric or zwitterionic surfactant is present in an amount ranging from about 0.1% to about 30% by weight, relative to the total weight of the composition.

9. The composition according to claim 1, wherein the at least one non-ionic surfactant is chosen from oxyalkylenated or glycerolated non-ionic surfactants, or mixtures thereof:
oxyalkylenated (C$_8$-C$_{24}$)alkylphenols;
saturated or unsaturated, linear or branched, oxyalkylenated or glycerolated C$_8$-C$_{30}$ alcohols;
saturated or unsaturated, linear or branched, oxyalkylenated C$_8$-C$_{30}$ fatty acid amides;
esters of saturated or unsaturated, linear or branched, C$_8$-C$_{30}$ acids and of polyethylene glycols;
esters of saturated or unsaturated, linear or branched, C$_8$-C$_{30}$ acids and of sorbitol;
fatty acid esters of sucrose;
(C$_8$-C$_{30}$)alkylpolyglycosides, (C$_8$-C$_{30}$)alkenylpolyglycosides, optionally oxyalkylenated (0 to 10 oxyalkylene units) and comprising 1 to 15 glucose units, (C$_8$-C$_{30}$) alkylglucoside esters;
oxyethylenated and saturated or unsaturated vegetable oils;
condensates of ethylene oxide and/or of propylene oxide, inter alis, alone or as mixtures;
N—(C$_8$-C$_{30}$)alkylglucamine derivatives and N—(C$_8$-C$_{30}$)acyl-methylglucamine derivatives;
aldobionamides;
amine oxides;
oxyethylenated and/or oxypropylenated silicones;
or mixtures thereof.

10. The composition according to claim 1, wherein the at least one non-ionic surfactant is present in an amount ranging from about 0.1% to about 30% by weight, relative to the total weight of the composition.

11. The composition according to claim 1, wherein the at least one anionic surfactant is chosen from alkyl sulfates, alkyl ether sulfates, alkylamido ether sulfates, alkylaryl polyether sulfates, monoglyceride sulfates, alkyl sulfonates, alkylamide sulfonates, alkylaryl sulfonates, alpha-olefin sulfonates, paraffin sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N-acyl taurates; salts of alkyl monoesters of polyglycoside-polycarboxylic acids, acyl lactylates, salts of D-galactoside uronic acids, salts of alkyl ether carboxylic acids, salts of alkylaryl ether carboxylic acids, salts of alkylamido ether carboxylic acids, and the corresponding non-salified forms thereof, and the alkyl and acyl groups thereof comprising from 6 to 40 carbon atoms, wherein the aryl group is a phenyl group.

12. The composition according to claim 1, wherein the at least one anionic surfactant is present in an amount ranging from about 0.1% to about 30% by weight, relative to the total weight of the composition.

13. The composition according to claim 1, wherein the at least one fatty substance is present in an amount ranging from about 15% to about 70% by weight, relative to the total weight of the composition.

14. The composition according to claim 1, wherein the at least one cationic polymer has a charge density of at least 1 meq/g.

15. The composition according to claim 1, wherein the at least one cationic polymer is chosen from the following polymers, alone or as mixtures:

(1) homopolymers or copolymers derived from acrylic or methacrylic esters or amides, and comprising at least one of the units of formula (I), (II), (III) or (IV) below:

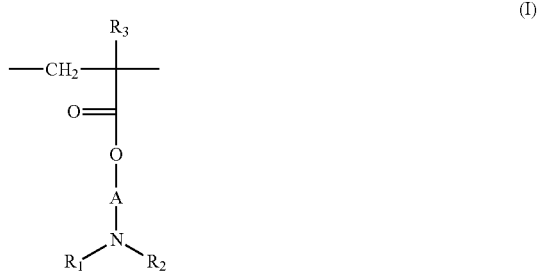

(I)

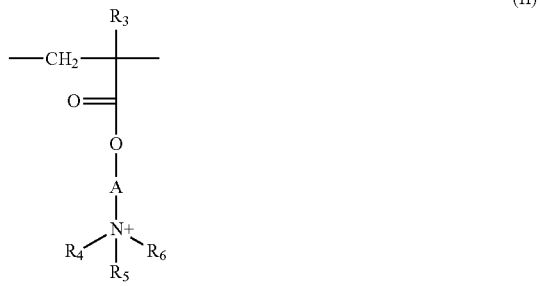

(II)

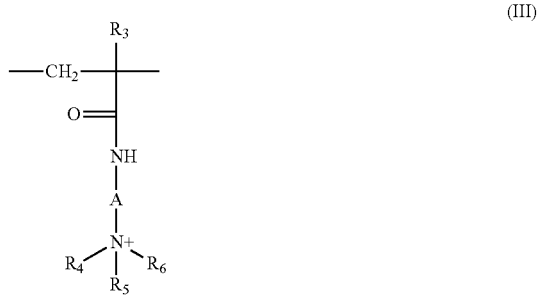

(III)

-continued

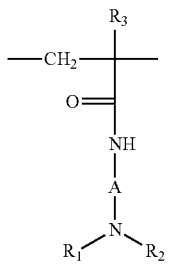

(IV)

wherein:
R$_3$, which may be identical or different, denote a hydrogen atom or a CH$_3$ radical;
A, which may be identical or different, represent a linear or branched C$_1$-C$_6$ alkyl group or a hydroxyalkyl group, the alkyl of which is C$_1$-C$_4$;
R$_4$, R$_5$ and R$_6$, which may be identical or different, are chosen from C$_1$-C$_{18}$ alkyl group or a benzyl radical;
R$_1$ and R$_2$, which may be identical or different, are chosen from hydrogen or C$_1$-C$_6$ alkyl group;

(2) cationic cellulose derivatives;
(3) cationic guar gums;
(4) polymers consisting of piperazinyl units and of linear or branched divalent alkyl or hydroxyalkyl radicals, optionally interrupted with oxygen, sulfur, or nitrogen atoms, or with aromatic or heterocyclic rings; or oxidation and/or quaternization products of these polymers;
(5) water-soluble polyaminoamides, optionally cross-linked;
(6) polymers obtained by reaction of a polyalkylene polyamine comprising two primary amine groups and at least one secondary amine group with a dicarboxylic acid;
(7) cyclopolymers of alkyldiallylamine or of dialkyldiallylammonium, in the form of homopolymers or copolymers containing, as main constituent of the chain, units corresponding to formula (V) or (VI):

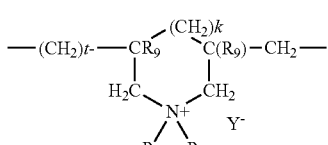

(V)

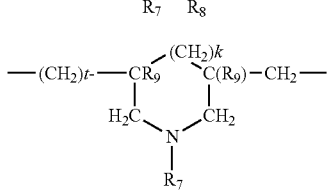

(VI)

wherein:
k and t are integers equal to 0 or 1, the sum k+t being equal to 1;
R$_9$ is a hydrogen atom or a methyl radical;
R$_7$ and R$_8$, independently of each other, are chosen from C$_1$-C$_8$ alkyl groups, hydroxyalkyl groups in which the alkyl group is C$_1$-C$_5$, or amidoalkyl groups in which the alkyl is C$_1$-C$_4$; or R$_7$ and R$_8$, together with the nitrogen atom to which they are attached, are chosen from heterocyclic groups; and
Y$^-$ is an organic or inorganic anion;
(8) diquaternary ammonium polymers containing repeating units corresponding to the formula:

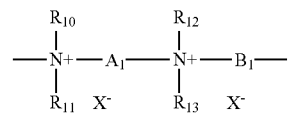

(VII)

wherein:
R$_{10}$, R$_{11}$, R$_{12}$ and R$_{13}$, which may be identical or different, are chosen from linear, branched or cyclic, saturated, unsaturated or aromatic, C$_1$-C$_{20}$ hydrocarbon-based radicals, linear or branched hydroxyalkyl radicals in which the alkyl part is C$_1$-C$_4$, or linear or branched C$_1$-C$_6$ alkyl radicals, substituted with nitrile, ester, acyl or amide groups or a group —CO—O—R$_{14}$-D or —CO—NH—R$_{14}$-D with R$_{14}$ chosen from alkyl radicals and D chosen from quaternary ammonium groups, or R$_{10}$, R$_{11}$, R$_{12}$ and R$_{13}$ form, together or separately, with the nitrogen atoms to which they are attached, heterocycles optionally containing a second heteroatom other than nitrogen;
A$_1$ and B$_1$ are chosen from linear or branched, saturated or unsaturated, C$_2$-C$_{20}$ radicals, optionally substituted with one or more aromatic rings, oxygen or sulfur atoms or groups bearing at least one of these atoms; and
X$^-$ is an organic or inorganic anion;
wherein A$_1$, R$_{10}$ and R$_{12}$ may optionally form, with the two nitrogen atoms to which they are attached, a piperazine ring; and
further wherein, if A$_1$ is chosen from a linear or branched, saturated or unsaturated alkylene or hydroxyalkylene radical, B$_1$ can also be chosen from a —(CH$_2$)$_n$CO-D-OC(CH$_2$)$_n$- group wherein n ranges from 1 to 100, and D is chosen from a glycol, bis-secondary diamine, bis-primary diamine or ureylene residue;
(9) polyquaternary ammonium polymers consisting of repeating units of formula (IX):

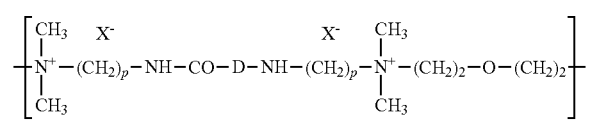

(IX)

wherein p is an integer ranging from 1 to 6, D may be zero or may be a —(CH$_2$)$_r$—CO- group in which r ranges from 4 to 7, and X$^-$ is an organic or inorganic anion;
(10) quaternary polymers of vinylpyrrolidone and of vinylimidazole; and
(11) polyamines.

16. The composition according to claim 1, wherein the at least one cationic polymer is present in an amount ranging from about 0.01% to about 10% by weight, relative to the weight of the composition.

17. A process for dyeing keratin fibers, comprising:
(a) preparing a dye composition by mixing:
- a first composition free of oxidizing agent other than atmospheric oxygen, comprising at least one coloring agent chosen from oxidation dye precursors, direct dyes and mixtures thereof; and
- a second composition comprising at least one oxidizing agent other than atmospheric oxygen;

wherein at least one of the first or second compositions comprises at least one fatty substance chosen from liquid paraffins, petroleum jelly, liquid petroleum jelly, Polvdecenes, or hydrogenated polyisobutene, at least one cationic polymer, and at least one amphoteric or zwitterionic surfactant;

wherein the resulting mixture has a total fatty substance content of at least about 10% by weight relative to the weight of the mixture;

wherein the amphoteric surfactant and anionic surfactant are present in a weight ratio ranging from 0.1 to 10; and (b) applying said dye composition to said keratin fibers.

18. A device for mixing and using a composition for dyeing keratin fibers, comprising:
- a first compartment containing a composition free of oxidizing agent other than atmospheric oxygen, comprising at least one coloring agent chosen from oxidation dye precursors, direct dyes or mixtures thereof; and
- a second compartment containing an oxidizing composition;

wherein at least one of the compositions comprises at least one fatty substance chosen from liquid paraffins, petroleum jelly, liquid petroleum jelly, polvdecenes, or hydrogenated polyisobutene, at least one cationic polymer, at least one amphoteric or zwitterionic surfactant, at least one anionic surfactant;

wherein the amphoteric surfactant and anionic surfactant are present in a weight ratio ranging from 0.1 to 10; and wherein the composition in the first compartment and the composition in the second compartment are mixed before use.

* * * * *